US010272248B2

(12) United States Patent
Engels et al.

(10) Patent No.: US 10,272,248 B2
(45) Date of Patent: Apr. 30, 2019

(54) ELECTROGRAM-BASED CONTROL OF CARDIAC RESYNCHRONIZATION THERAPY

(71) Applicants: Medtronic, Inc., Minneapolis, MN (US); Universiteit Maastricht, Maastricht OT (NL); Academisch Ziekenhuis Maastricht, Maastricht OT (NL)

(72) Inventors: Elien B. Engels, Maastricht (NL); Kevin Vernooy, Maastricht (NL); Alfonso Aranda Hernandez, Maastricht (NL); Frits W. Prinzen, Maastricht (NL); Jeffrey M. Gillberg, Coon Rapids, MN (US)

(73) Assignees: Medtronic, Inc., Minneapolis, MN (US); Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 15/610,231

(22) Filed: May 31, 2017

(65) Prior Publication Data
US 2017/0340887 A1    Nov. 30, 2017

Related U.S. Application Data

(60) Provisional application No. 62/343,787, filed on May 31, 2016, provisional application No. 62/343,796, filed on May 31, 2016.

(51) Int. Cl.
*A61N 1/39*    (2006.01)
*A61N 1/365*    (2006.01)
(Continued)

(52) U.S. Cl.
CPC .......... *A61N 1/3682* (2013.01); *A61B 5/0468* (2013.01); *A61B 5/0472* (2013.01);
(Continued)

(58) Field of Classification Search
CPC .............. A61N 1/36592; A61N 1/3682; A61N 1/36521; A61N 1/3962; A61N 1/3684;
(Continued)

(56) References Cited

U.S. PATENT DOCUMENTS 5,843,141 A    12/1998  Bischoff et al.
5,954,660 A     9/1999  Legay et al.
(Continued)

OTHER PUBLICATIONS

Van Deursen et al., "Vectorcardiography as a Tool for Easy Optimization of CRT in Caine LBBB Hearts", 2011, Circ Arrhythmia. Electrophysisol, pp. 544-552.*
(Continued)

*Primary Examiner* — Catherine M Voorhees
(74) *Attorney, Agent, or Firm* — Shumaker & Sieffert, P.A.

(57) ABSTRACT

In some examples, controlling delivery of CRT includes delivering ventricular pacing according to a sequence of different values of at least one of A-V delay or V-V delay, and acquiring one or more electrograms from respective vectors. For each of the different values of the at least one of A-V delay or V-V delay, at least one of a QRS amplitude or a QRS area may be determined based on the one or more electrograms, and a target change in QRS amplitude or QRS area between adjacent ones of the values of the at least one of A-V delay or V-V delay of the sequence may be identified. In response to the identification of the target change, the implantable medical device may deliver the ventricular pacing at a value of the at least one of A-V delay or V-V delay determined based on the identification to provide CRT.

22 Claims, 14 Drawing Sheets

(51) Int. Cl.
- *A61N 1/368* (2006.01)
- *A61N 1/372* (2006.01)
- *A61B 5/0468* (2006.01)
- *A61B 5/0472* (2006.01)

(52) U.S. Cl.
CPC ......... *A61N 1/3684* (2013.01); *A61N 1/3686* (2013.01); *A61N 1/36521* (2013.01); *A61N 1/36564* (2013.01); *A61N 1/36592* (2013.01); *A61N 1/37217* (2013.01); *A61N 1/3956* (2013.01); *A61N 1/3962* (2013.01)

(58) Field of Classification Search
CPC .............. A61N 1/37217; A61N 1/3686; A61N 1/36564; A61N 1/3956; A61B 5/0468; A61B 5/0472
See application file for complete search history.

(56) References Cited

U.S. PATENT DOCUMENTS

| | | |
|---|---|---|
| 6,178,344 B1 | 1/2001 | Hull et al. |
| 6,370,423 B1 | 4/2002 | Guerrero et al. |
| 6,567,704 B2 | 5/2003 | Sundquist et al. |
| 6,643,549 B1 | 11/2003 | Bradley et al. |
| 6,743,227 B2 | 6/2004 | Seraj et al. |
| 6,799,991 B2 | 10/2004 | Williams et al. |
| 6,832,112 B1 | 12/2004 | Bornzin |
| 6,854,994 B2 | 2/2005 | Stein et al. |
| 6,901,289 B2 | 5/2005 | Dahl et al. |
| 6,968,235 B2 | 11/2005 | Belden et al. |
| 6,978,178 B2 | 12/2005 | Sommer et al. |
| 7,076,309 B2 | 7/2006 | Hine et al. |
| 7,087,017 B2 | 8/2006 | Christopherson et al. |
| 7,092,759 B2 | 8/2006 | Nehls et al. |
| 7,107,093 B2 | 9/2006 | Burnes |
| 7,139,610 B2 | 11/2006 | Ferek-Petric |
| 7,181,284 B2 | 2/2007 | Burnes et al. |
| 7,239,916 B2 | 7/2007 | Thompson et al. |
| 7,254,450 B2 | 8/2007 | Christopherson et al. |
| 7,287,995 B2 | 10/2007 | Stein et al. |
| 7,532,939 B2 | 5/2009 | Sommer et al. |
| 7,558,626 B2 | 7/2009 | Corbucci |
| 7,623,053 B2 | 11/2009 | Terry et al. |
| 7,672,733 B2 | 3/2010 | Zhou et al. |
| 7,783,365 B2 | 8/2010 | Ebert et al. |
| 7,846,095 B2 | 12/2010 | Christopherson et al. |
| 8,005,544 B2 | 8/2011 | Zhu et al. |
| 8,019,420 B2 | 9/2011 | Hine et al. |
| 8,065,008 B2 | 11/2011 | Sommer et al. |
| 8,086,200 B2 | 12/2011 | Sutton et al. |
| 8,209,032 B2 | 6/2012 | Ebert et al. |
| 8,214,045 B2 | 7/2012 | Kronich et al. |
| 8,233,994 B2 | 7/2012 | Sommer et al. |
| 8,295,943 B2 | 10/2012 | Eggen et al. |
| 8,326,418 B2 | 12/2012 | Sommer et al. |
| 8,332,045 B2 | 12/2012 | Sommer et al. |
| 8,417,337 B2 | 4/2013 | Busacker et al. |
| 8,428,528 B2 | 4/2013 | Sutton et al. |
| 8,437,856 B2 | 5/2013 | Sommer et al. |
| 8,509,893 B2 | 8/2013 | Xiao et al. |
| 8,587,426 B2 | 11/2013 | Bloem |
| 8,615,298 B2 | 12/2013 | Ghosh et al. |
| 8,630,719 B2 | 1/2014 | Eggen et al. |
| 8,639,340 B2 | 1/2014 | Sommer et al. |
| 8,639,341 B2 | 1/2014 | Sommer et al. |
| 8,744,572 B1 | 6/2014 | Greenhut et al. |
| 8,825,180 B2 | 9/2014 | Bauer et al. |
| 8,923,963 B2 | 12/2014 | Bonner et al. |
| 9,037,237 B2 | 5/2015 | Fischer et al. |
| 9,248,294 B2 | 2/2016 | Prinzen et al. |
| 9,375,580 B2 | 6/2016 | Bonner et al. |
| 2001/0044624 A1 | 11/2001 | Seraji et al. |
| 2002/0077685 A1 | 6/2002 | Sundquist et al. |
| 2002/0111662 A1 | 8/2002 | Iaizzo et al. |
| 2002/0111663 A1 | 8/2002 | Dahl et al. |
| 2002/0173785 A1 | 11/2002 | Spear et al. |
| 2003/0018364 A1 | 1/2003 | Belden et al. |
| 2003/0018369 A1 | 1/2003 | Thompson et al. |
| 2003/0077935 A1 | 4/2003 | Stein et al. |
| 2003/0083586 A1 | 5/2003 | Ferek-Petric |
| 2003/0204234 A1 | 10/2003 | Hine et al. |
| 2003/0216800 A1 | 11/2003 | Ebert et al. |
| 2004/0078067 A1 | 4/2004 | Thompson et al. |
| 2004/0087847 A1 | 5/2004 | Christopherson et al. |
| 2004/0176822 A1 | 9/2004 | Thompson et al. |
| 2004/0199082 A1 | 10/2004 | Ostroff et al. |
| 2004/0215252 A1 | 10/2004 | Verbeek et al. |
| 2004/0215299 A1 | 10/2004 | Zhao et al. |
| 2005/0020895 A1 | 1/2005 | Christopherson et al. |
| 2005/0021120 A1 | 1/2005 | Christopherson et al. |
| 2005/0033371 A1 | 2/2005 | Sommer et al. |
| 2005/0065570 A1 | 3/2005 | Stein et al. |
| 2005/0229693 A1 | 10/2005 | Bauer et al. |
| 2006/0235478 A1* | 10/2006 | Van Gelder .......... A61N 1/3627 607/9 |
| 2007/0299490 A1 | 12/2007 | Yang et al. |
| 2008/0039900 A1 | 2/2008 | Stein et al. |
| 2009/0054936 A1 | 2/2009 | Eggen et al. |
| 2009/0054941 A1 | 2/2009 | Eggen et al. |
| 2009/0054946 A1 | 2/2009 | Sommer et al. |
| 2009/0079606 A1 | 3/2009 | Terry et al. |
| 2009/0131873 A1 | 5/2009 | Spear et al. |
| 2009/0177110 A1 | 7/2009 | Lyden et al. |
| 2009/0192581 A1 | 7/2009 | Sommer et al. |
| 2009/0234405 A1 | 9/2009 | Sommer et al. |
| 2009/0234412 A1 | 9/2009 | Sambelashvili |
| 2009/0234414 A1 | 9/2009 | Sambelashvili et al. |
| 2009/0276004 A1 | 11/2009 | Kronich et al. |
| 2009/0306752 A1 | 12/2009 | Ebert et al. |
| 2010/0113943 A1 | 5/2010 | Burnes et al. |
| 2010/0114282 A1 | 5/2010 | Ebert et al. |
| 2010/0198311 A1 | 8/2010 | Sommer et al. |
| 2010/0256701 A1* | 10/2010 | Muller ................. A61B 5/0452 607/14 |
| 2010/0262204 A1 | 10/2010 | McCabe et al. |
| 2011/0004117 A1 | 1/2011 | Neville et al. |
| 2011/0029034 A1 | 2/2011 | Fischer et al. |
| 2012/0109237 A1 | 5/2012 | Xiao et al. |
| 2012/0130466 A1 | 5/2012 | Sommer et al. |
| 2012/0136422 A1 | 5/2012 | Ebert et al. |
| 2012/0165902 A1 | 6/2012 | Sommer et al. |
| 2012/0190991 A1 | 7/2012 | Bomzin et al. |
| 2013/0030314 A1 | 1/2013 | Keel et al. |
| 2013/0030487 A1 | 1/2013 | Keel et al. |
| 2013/0035738 A1 | 2/2013 | Karst et al. |
| 2013/0046369 A1 | 2/2013 | Eggen et al. |
| 2013/0325086 A1 | 12/2013 | Sommer et al. |
| 2014/0121719 A1 | 5/2014 | Bonner et al. |
| 2014/0121720 A1 | 5/2014 | Bonner et al. |
| 2014/0277233 A1 | 9/2014 | Ghosh |
| 2014/0330208 A1 | 11/2014 | Christie et al. |
| 2014/0330248 A1 | 11/2014 | Thompson-Nauman et al. |
| 2014/0330326 A1 | 11/2014 | Thompson-Nauman et al. |
| 2015/0080981 A1 | 3/2015 | John |
| 2015/0142069 A1* | 5/2015 | Sambelashvili ..... A61N 1/3688 607/18 |
| 2015/0202443 A1 | 7/2015 | Zielinski et al. |

OTHER PUBLICATIONS

Engels et al., "Tailoring device settings in cardiac resynchronization therapy using electrograms from pacing electrodes", Feb. 23, 2017, Europace (2017) 0, pp. 1-8.*

Engles, et al., "Tailoring device settings in cardiac resynchronization therapy using electrograms from pacing electrodes," Eurospace, May 2017, 8 pp.

Engels, "Something old, something new; Vectorcardiographic loop size and response to cardiac resynchronization therapy," Oct. 2016, 204 pp.

"Abstracts," Heart Rhythm, vol. 14, No. 5, May Supplement 2017, S1-S668, 93 pp.

(56) References Cited

OTHER PUBLICATIONS

Europace Abstract Supplement, Poster Session 3, Jun. 20, 2017, 2 pp.
International Preliminary Report on Patentability from International Application No. PCT/US2017/035287, dated May 8, 2018, 7 pp.
Gasparini et al. "Comparison of 1-year effects of left ventricular and biventricular pacing in patients with heart failure who have ventricular arrhythmias and left bundle-branch block: The Bi vs Left Ventricular Pacing: An International Pilot Evaluation on Heart Failure Patients with Ventricular Arrhythmias (BELIEVE) multi-center prospective randomized pilot study," Am Heart J. 2006, accepted Apr. 3, 2006, pp. 154-155.e7.
Boriani, et al. "A randomized double-blind comparison of biventricular versus left ventricular stimulation for cardiac resynchronization therapy: the Biventricular versus Left Univentricular Pacing with ICD Back-up in Heart Failure Patients (B-LEFT HF) trial." Am Heart J. 2010;159(6), accepted Mar. 4, 2010, pp. 1052-1058.e1.
Strik MD et al. "Interplay of electrical wavefronts as determinant of the response to cardiac resynchronization therapy in dys-synchronous canine hearts," Circulation Arrhythmia and electrophysiology. 2013;6(5), accepted Sep. 11, 2013, pp. 924-931.
Martin MD MPH, et al. "Investigation of a novel algorithm for synchronized left-ventricular pacing and ambulatory optimization of cardiac resynchronization therapy: results of the adaptive CRT trial," Heart Rhythm. Nov. 2012;9(11):1807-14.
Strauss MD, PhD, et al.,. "Defining left bundle branch block in the era of cardiac resynchronization therapy." Am J Cardiol. 2011;107(6): Mar. 15, 2011; pp. 927-934.
Ghafoori MS et al., "Construction of intracardiac vectorcardiogram from implantable cardioverter-defibrillator intracardiac electrograms," J Electrocardiol., Jul.-Aug. 2015;48(4); pp. 669-671.
Khaykin, "Adjusting the timing of left-ventricular pacing using electrocardiogram and device electrograms," Europace. 2011;13(10); accepted Apr. 14, 2011, pp. 1464-1470.
Bogaard MD, et al. "Baseline left ventricular dP/dtmax rather than the acute improvement in dP/dtmax predicts clinical outcome in patients with cardiac resynchronization therapy," Eur J Heart Fail. 2011;13(10); accepted May 27, 2011, pp. 1126-1132.
Ponikowski, et al. "2016 ESC Guidelines for the diagnosis and treatment of acute and chronic heart failure: The Task Force for the diagnosis and treatment of acute and chronic heart failure of the European Society of Cardiology (ESC)," Developed with the special contribution of the Heart Failure Association (HFA) of the ESC. Eur J Heart Fail., Jul. 14, 2016;18(8): pp. 891-975.
International Search Report and Written Opinion from International Application No. PCT/US2017/035287, dated Jul. 27, 2017, 16 pp.
Response to Written Opinion dated Jul. 27, 2017, from International Application No. PCT/US2017/035287, filed on Mar. 9, 2018, 12 pp.
Van Deursen et al., "Vectorcardiography as a tool for easy optimization of cardiac resynchronization in canine LBBB hearts", Circ. Arrhythm. Electrophysiol, Jun. 2012; 5: pp. 544-522.
Cleland, et al., "The Effect of Cardiac Resynchronization on Morbidity and Morality in Heart Failure," N. Engl J. Med, 352(15), Apr. 14, 2005, pp. 1539-1549.
Daubert, et al. "2012 EHRA/HRS expert consensus statement on cardiac resynchronization therapy in heart failure: implant and follow-up recommendations and management," EHRA/HRS Statement on Cardiac Resynchronization Therapy, Heart Rhythm, 9(9), Jul. 2012, pp. 1524-1576.
Mullens, MD et al., Insights from a cardiac resynchronization optimization clinic as part of a heart failure disease management program. J Am Coll Cardiol, vol. 53, (9), Mar. 3, 2009, pp. 765-773.
Vernooy, MD., et al., "Calculation of effective VV interval facilitates optimization of AV delay and VV interval in cardiac resynchronization therapy," Heart Rhythm, 4(1), accepted Sep. 7, 2006, pp. 75-82.
Strik, et al. (2013). Interplay of electrical wavefronts as determinant of the response to cardiac resynchronization therapy in dys-synchronous canine hearts. Circ Arrhythm Electrophysiol, 6(5), Sep. 11, 2013, 924-931.

Ellenbogen, MD et al., "Primary results from the SmartDelay determined AV optimization: a comparison to other AV delay methods used in cardiac resynchronization therapy (SMART-AV) trial: a randomized trial comparing empirical, echocardiography-guided, and algorithmic atrioventricular delay programming in cardiac resynchronization therapy." Circulation, Oct. 22, 2010, 122(25), 2660-2668.
Auricchio, MD et al. "Effect of pacing chamber and atrioventricular delay on acute systolic function of paced patients with congestive heart failure" The Pacing Therapies for Congestive Heart Failure Study Group. The Guidant Congestive Heart Failure Research Group., Circulation, 99(23), Dec. 21, 2010, pp. 2993-3001.
Auricchio, MD et al. "The Pacing Therapies for Congestive Heart Failure (PATH-CHF) study: rationale, design, and endpoints of a prospective randomized multicenter study." Am J Cardiol, 83(5B), Mar. 11, 1999, pp. 130D-135D.
Kass, MD et al. "Improved left ventricular mechanics from acute VDD pacing in patients with dilated cardiomyopathy and ventricular conduction delay," Circulation, 99(12), Dec. 1998; pp. 1567-1573.
Whinnett, et al. "Determination of optimal atrioventricular delay for cardiac resynchronization therapy using acute non-invasive blood pressure," Europace, 8(5), revision Feb. 2006, pp. 358-366.
Butter, MD, et al., "Cardiac resynchronization therapy optimization by finger plethysmography," Heart Rhythm, 1(5), accepted Jul. 2, 2004, pp. 568-575.
Ritter, et al. "A randomized pilot study of optimization of cardiac resynchronization therapy in sinus rhythm patients using a peak endocardial acceleration sensor vs. standard methods," Europace, 14(9), published online May 2012; pp. 1324-1333.
Gold, MD., Ph.D., et al "A prospective comparison of AV delay programming methods for hemodynamic optimization during cardiac resynchronization therapy," J Cardiovasc Electrophysiol, 18(5), accepted Dec. 29, 2006, pp. 490-496.
Baker III, MD, et al. "Acute evaluation of programmer-guided AV/PV and VV delay optimization comparing an IEGM method and echocardiogram for cardiac resynchronization therapy in heart failure patients and dual-chamber ICD implants," J Cardiovasc Electrophysiol, 18(2), Feb. 2007, pp. 185-191.
Krum, MBBS, PhD, et al. "A novel algorithm for individualized cardiac resynchronization therapy: rationale and design of the adaptive cardiac resynchronization therapy trial," Am Heart J, 163(5), May 2012; pp. 747-752 e741.
Van Gelder, PhD., et al. "The hemodynamic effect of intrinsic conduction during left ventricular pacing as compared to biventricular pacing," J Am Coll Cardiol, vol. 46(12), accepted Feb. 1, 2005, pp. 2305-2310.
Van Deursen, MD., et al. "Vectorcardiography for optimization of stimulation intervals in cardiac resynchronization therapy," J Cardiovasc Transl Res, 8(2), published online Mar. 6, 2015, pp. 128-137.
Van Deursen, MD., et al. "Vectorcardiography as a tool for easy optimization of cardiac resynchronization therapy in canine left bundle branch block hearts," Circ Arrhythm Electrophysiol, 5(3), Jun. 2012; pp. 544-552.
Engels, Ph.D., et al., "Prediction of optimal cardiac resynchronization by vectorcardiography in dyssynchronous canine hearts," Journal of Cardiovascular Electrophysiology, May 3, 2017, 19 pp.
Brignole, et al., "2013 ESC Guidelines on cardiac pacing and cardiac resynchronization therapy: the Task Force on cardiac pacing and resynchronization therapy of the European Society of Cardiology (ESC). Developed in collaboration with the European Heart Rhythm Association (EHRA)," Eur Heart J, 34(29), Jun. 24, 2003, pp. 2281-2329.
Whinnett, et al. "Haemodynamic effects of changes in atrioventricular and interventricular delay in cardiac resynchronisation therapy show a consistent pattern: analysis of shape, magnitude and relative importance of atrioventricular and interventricular delay," Cardiovascular Medicine, Heart, 92(11), published online May 18, 2006, pp. 1628-1634.
Kors, et al,. "Reconstruction of the Frank vectorcardiogram from standard electrocardiographic leads: diagnostic comparison of different methods," Eur Heart J, 11(12), revised form Mar. 12, 1990, pp. 1083-1092.

(56) References Cited

OTHER PUBLICATIONS

Engels, et al., "T-wave area predicts response to cardiac resynchronization therapy in patients with left bundle branch block." J Cardiovasc Electrophysiol, 26(2), accepted Sep. 2, 2014, pp. 176-183.

Bogaard, et al. "Baseline left ventricular dP/dtmax rather than the acute improvement in dP/dtmax predicts clinical outcome in patients with cardiac resynchronization therapy," Eur J Heart Fail, 13(10), published online Jul. 26, 2011, pp. 1126-1132.

Padeletti, et al., "Simultaneous His Bundle and Left Ventricular Pacing for Optimal Cardiac Resynchronization Therapy Deliver," Acute Hemodynamic Assessment by Pressure—Volume Loops, Circulation: Arrhythmia and Electrophysiology, May 9, 2016, 9 pp.

* cited by examiner

FIG. 10A         FIG. 10B
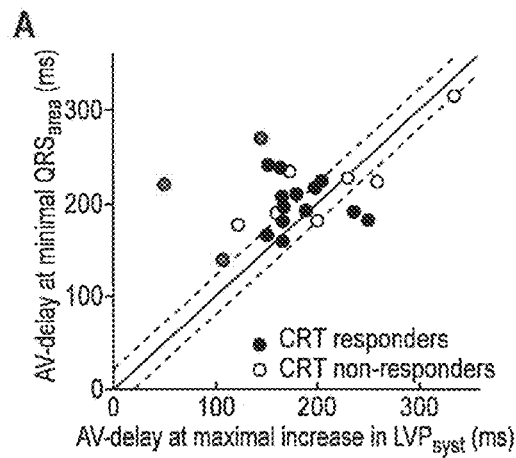         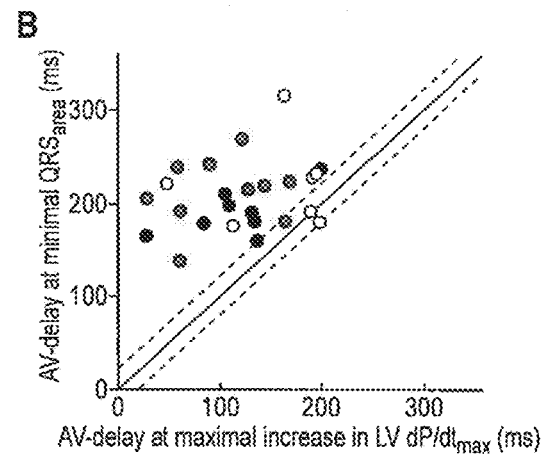
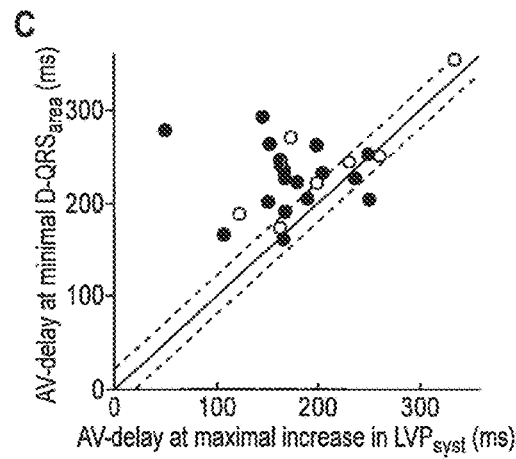         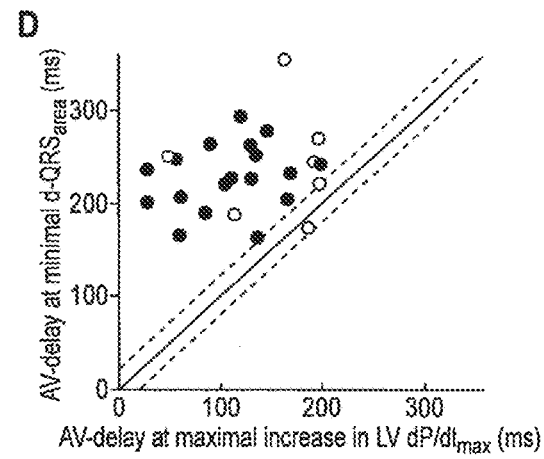
FIG. 10C         FIG. 10D

FIG. 12A 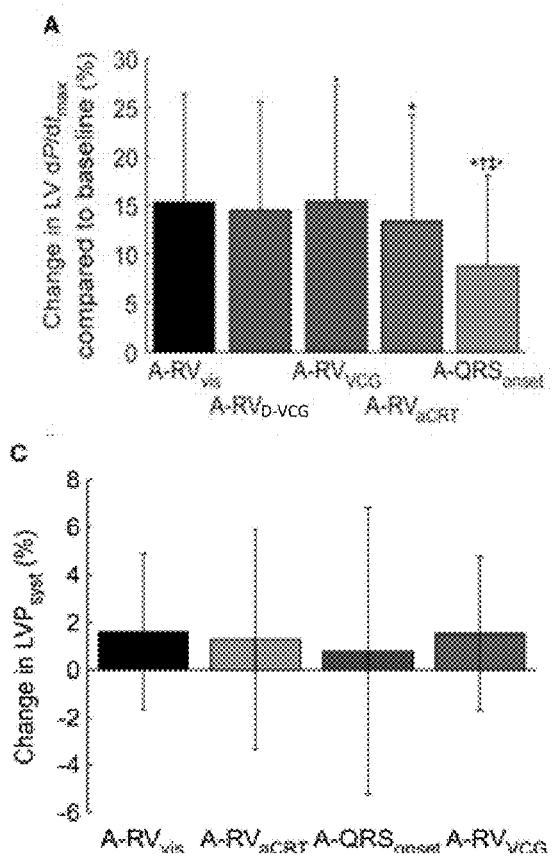 FIG. 12B 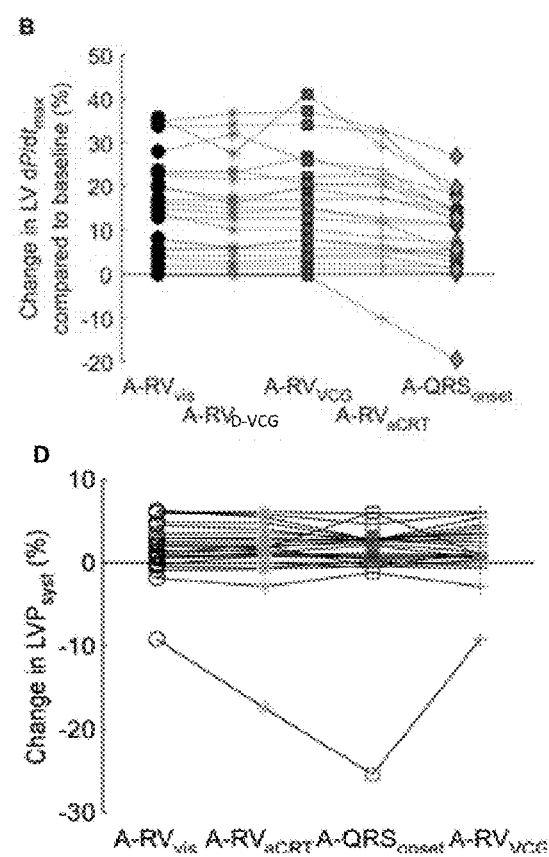
FIG. 12C
FIG. 12D

ELECTROGRAM-BASED CONTROL OF CARDIAC RESYNCHRONIZATION THERAPY

This application claims the benefit of U.S. Provisional Application Ser. Nos. 62/343,787 and 62/343,796, filed May 31, 2016, the entire contents of each of which are incorporated herein by reference.

TECHNICAL FIELD

The present disclosure relates to implantable cardiac pulse generators (IPGs) generally, and more particularly to implantable cardioverters defibrillators (ICDs) and triple-chamber pacing devices configured to deliver cardiac resynchronization therapy (CRT).

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device may sense intrinsic depolarizations of the heart, and control the delivery of therapeutic stimulation to the heart based on the sensing.

Cardiac resynchronization therapy (CRT) is one type of therapy delivered by an implantable medical device. Cardiac resynchronization therapy may help enhance cardiac output by resynchronizing the electromechanical activity of the ventricles of the heart. Ventricular desynchrony may occur in patients that suffer from heart failure (HF).

CRT is one of the most successful heart failure (HF) therapies to emerge in the last 25 years and is applicable to 25-30% of patients with symptomatic HF, especially those with abnormal impulse conduction through the ventricles, such as left bundle branch block (LBBB). Since initial approval of the therapy over 10 years ago, there have been hundreds of thousands of implants worldwide. Although the effects of CRT on the population level are impressive, benefits at the individual level vary considerably. Depending on the definition, the response to CRT is positive in 50-70% of patients, leaving 30-50% without significant effect. Such lack of response is especially not desirable, since CRT requires the virtually irreversible implantation of a costly device and pacing electrodes during an invasive procedure.

Effectiveness of CRT can be improved by optimal programming of the device, especially with regard to the time delay (A-V delay) between activation (e.g., intrinsic or in response to electrical stimulation) of the right atrium (RA) and electrical stimulation of the ventricles and the time delay (V-V interval) between activation of the right ventricle (RV) and stimulation of the left ventricle (LV). Such CRT optimization increases acute hemodynamic benefits of CRT by 20-30% and improves short-term clinical response. In half of CRT clinical non-responders it is believed that symptoms could be improved by careful A-V interval and V-V interval optimization. However, in regular clinical practice, "out-of-the-box" default settings are often used for these intervals. Furthermore, echocardiographic techniques can be used to optimize A-V and V-V intervals, but such optimization procedures are relatively complicated procedures and the echocardiographic measurements are notoriously inaccurate. A further serious limitation of echocardiographic optimization is that it is performed in the recumbent position in full rest, while optimization is likely more required under more conditions of higher physical activity.

Evidence has been collected in animal experiments and CRT patients that the QRS complex in the vectorcardiogram (VCG), measured at the body surface, provides an accurate description of the degree of resynchronization during the various AV- and VV-intervals. The results of this study are presented in "Vectorcardiography as a tool for easy optimization of cardiac resynchronization in canine LBBB hearts"; Van Deursen, et al, Circ. Arrhythm. Electrophysiol, 2012; 5:544-522, incorporated herein by reference in its entirety. This study also showed that accuracy of QRS vector determination is considerably higher than that of hemodynamic measurements.

Subsequently, in a group of 11 patients, it was observed that the best hemodynamic response ("$VTI_{LVOT}$") and the most physiological contraction pattern (minimal value of SPS+SRS) occur at A-V and V-V intervals where the three-dimensional area of the QRS-complex on the VCG loop (QRSVarea) is minimal. This observation is described, for example, U.S. Pat. No. 9,248,294 B2 to Prinzen et al., issued Feb. 2, 2016, the disclosure of which is incorporated by reference in its entirety herein. This minimal QRS-area, which can be determined using surface ECG measurements, provides an easy and accurate index for initial programming of optimal A-V and V-V intervals. FIG. 1 of U.S. Pat. No. 9,248,294 B2 illustrated the use of a surface VCG for optimization of CRT, showing data from a representative CRT patient. The A-V delay at which QRSV area was minimal coincided with the A-V delay where a minimal value was found for the sum of septal systolic pre-stretch (SPS) and rebound stretch (SRS; indicating the least abnormal septal contraction) as well as the highest value of $VTI_{LVOT}$ (~stroke volume). In 11 patients, the difference between actual maximal increase in $VTI_{LVOT}$ relative to LBBB and VCG-predicted increase was small (−0.4%; IR −1.6 to 0% and −0.5%; IR −1.3 to −0.2% respectively). Surface VCGs thus provide a useful tool in conjunction with both initial implant and later follow-up visits for adjustment of stimulation parameters.

In this prior study, the inventors also found that the measured surface QRS vector amplitude also could be used to optimize A-V and V-V delays. In this case, the combination of A-V and V-V intervals that produced a surface QRS vector amplitude halfway between that seen during LV pacing at short A-V intervals and that seen during un-paced LBBB rhythm corresponded to minimal QRSV area and to optimal hemodynamic performance.

SUMMARY

In general, this disclosure is directed to techniques for controlling the delivery of CRT. Such techniques may include determining one or both of an A-V delay and a V-V delay, and delivering fusion pacing therapy to one of the ventricles, such as the left ventricle, or biventricular pacing therapy based on the determined interval. In order to obtain adequate synchronization of ventricular activation, e.g., fusion of ventricular pacing with the intrinsic activation of the non-paced ventricle in some examples, one or more parameters for CRT pacing, such as an A-V delay or a V-V delay, may approximate a patient-specific value. In some examples, a patient-specific value of an A-V delay may be obtained from a visual examination of an ECG during fusion pacing, which may be done shortly after implantation of the CRT device or at another clinician visit.

However, determination of a patient-specific A-V delay based on a visual examination of an ECG is limited to clinical or hospital settings. Thus, in such examples, CRT may be delivered according to the same A-V delay between clinician visits, which may be weeks or months apart. As the patient's disease state evolves, for example, due to an acute HF decompensation event or because of deleterious remodeling that occurs in the progression of HF or otherwise during the course of HF treatment and therapy, the optimal A-V delay may change between physician visits. A similar condition may arise during physical exercise, when conduction properties of the heart may change due to activation of the sympathetic and parasympathetic nervous system. Since the patient-specific A-V delay may fluctuate or change on a more frequent basis, such as over the course of a day, similarly frequent updates to the A-V delay by which CRT is delivered may be associated with improved patient outcome. Consequently, A-V delay optimization would benefit from a closed loop method and apparatus for adapting to same.

Accordingly, techniques described herein may include determining an appropriate A-V delay by delivering CRT at varying A-V delays and determining whether an amplitude of a QRS complex of one or more electrograms generated by one or more vectors formed by implanted electrodes changes in response. In some examples, the minimal value of the area of the QRS complex of one or more electrograms generated by one or more vectors formed by implanted electrodes is used to optimize A-V and V-V delays during biventricular pacing. In this manner, an appropriate A-V delay and/or V-V delay for CRT may be determined by approximating the patient-specific delay on a frequent basis, such as daily or even semi-continuously.

For repetitive adjustment of A-V and V-V delays to varying conditions (e.g., sleep, exercise, myocardial remodeling due the therapy, or altering disease process) the principle of the optimization can be extended to a VCG derived from the implanted device and its connected electrodes rather than the body surface ECG. Such vectorcardiogram is hereafter referred to as "D-VCG" and may comprise a two-dimensional or three dimensional VCG. A D-VCG may also be referred to as an EGM-based vectorloop (EGMV) derived from EGMs of, in examples according to this disclosure, implanted electrodes. The electrodes can be subcutaneous electrodes or intravascular electrode, which may be carried on an implantable lead or a device housing.

The present invention provides more accurate pacing data for each patient since average data from multiple patients is not relied upon for updating pacing algorithms implemented by the processor of an implantable medical device. Additionally, the present disclosure also takes into account RV electrodes. Moreover, the invention continuously adapts to conditions such as exercise, sleep, worsening or improving cardiac function.

In one example, a method for controlling delivery of cardiac resynchronization therapy (CRT) by an implantable medical device of a medical device system comprises, by one or more processors of the medical device system: controlling the implantable medical device to deliver ventricular pacing according to a sequence of different values of at least one of A-V delay or V-V delay; during the delivery of ventricular pacing according to the sequence, acquiring one or more electrograms, each of the one or more electrograms from a respective one of a plurality of vectors formed by a plurality of electrodes of the medical device system; for each of the different values of the at least one of A-V delay or V-V delay, determining at least one of a QRS amplitude or a QRS area based on the one or more electrograms; identifying a target change in QRS amplitude or QRS area between adjacent ones of the values of the at least one of A-V delay or V-V delay of the sequence; and in response to the identification of the target change, controlling the implantable medical device to deliver the ventricular pacing at a value of the at least one of A-V delay or V-V delay determined based on the identification of the target change to provide CRT.

In another example, a medical device system for controlling delivery of cardiac resynchronization therapy (CRT) comprises therapy delivery circuitry configured to deliver ventricular pacing to a heart of a patient; sensing circuitry configured to sense electrical activity of the heart via a plurality of electrodes; and one or more processors configured to control the therapy delivery circuitry to deliver the ventricular pacing according to a sequence of different values of at least one of A-V delay or V-V delay; during the delivery of ventricular pacing according to the sequence, control the sensing circuitry to acquire one or more electrograms, each of the one or more electrograms from a respective one of a plurality of vectors formed by the plurality of electrodes; for each of the different values of the at least one of A-V delay or V-V delay, determine at least one of a QRS amplitude or a QRS area based on the one or more electrograms; identify a target change in QRS amplitude or QRS area between adjacent ones of the values of the at least one of A-V delay or V-V delay of the sequence; and in response to the identification of the target change, control the therapy delivery circuitry to deliver the ventricular pacing at a value of the at least one of A-V delay or V-V delay determined based on the identification of the target change to provide CRT.

In another example, an implantable medical device system for controlling delivery of left-ventricular fusion pacing comprises therapy delivery circuitry configured to deliver left-ventricular pacing to a heart of a patient; sensing circuitry configured to sense electrical activity of the heart via a plurality of implantable electrodes; and one or more processors configured to control the therapy delivery circuitry to deliver the left-ventricular pacing according to a sequence of different values of A-LV delay; during the delivery of the left-ventricular pacing according to the sequence, control the sensing circuitry to acquire a plurality of electrograms, each of the electrograms from a respective one of a plurality of vectors formed by the plurality of electrodes; determine a vectorcardiogram from the electrograms; for each of the different values of A-LV delay, determine a QRS amplitude based on the vectorcardiogram; identify a decrease in QRS amplitude between adjacent ones of the values of A-LV delay of the sequence, wherein the decrease in QRS amplitude indicates fusion occurring between the right and left ventricles; and in response to the identification of the decrease, control the therapy delivery circuitry to deliver the left-ventricular pacing at the shorter of the adjacent ones of the values of A-LV delay to provide CRT.

In another example, a system for controlling delivery of cardiac resynchronization therapy (CRT) comprises means for delivering ventricular pacing according to a sequence of different values of at least one of A-V delay or V-V delay; means for, during the delivery of ventricular pacing according to the sequence, acquiring one or more electrograms, each of the one or more electrograms from a respective one of a plurality of vectors formed by a plurality of electrodes of the medical device system; means for, for each of the different values of the at least one of A-V delay or V-V delay, determining at least one of a QRS amplitude or a QRS area based on the one or more electrograms; means for identifying a target change in QRS amplitude or QRS area between adjacent ones of the values of the at least one of A-V delay or V-V delay of the sequence; and means for, in response to the identification of the target change, delivering the ventricular pacing at a value of the at least one of A-V delay or V-V delay determined based on the identification of the target change to provide CRT.

In another example, a non-transitory computer-readable medium storing instructions for causing a processor of an implantable medical device system to perform a method for controlling delivery of cardiac resynchronization therapy (CRT), the method comprising controlling the implantable medical device to deliver ventricular pacing according to a sequence of different values of at least one of A-V delay or V-V delay; during the delivery of ventricular pacing according to the sequence, acquiring one or more electrograms, each of the one or more electrograms from a respective one of a plurality of vectors formed by a plurality of electrodes of the medical device system; for each of the different values of the at least one of A-V delay or V-V delay, determining at least one of a QRS amplitude or a QRS area based on the one or more electrograms; identifying a target change in QRS amplitude or QRS area between adjacent ones of the values of the at least one of A-V delay or V-V delay of the sequence; in response to the identification of the target change, controlling the implantable medical device to deliver the ventricular pacing at a value of the at least one of A-V delay or V-V delay determined based on the identification of the target change to provide CRT.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIGS. 10A-10D are graphical illustrations of VCG or D-VCG derived QRS areas indicative of an AV-delay resulting in high LV systolic pressure;

FIGS. 12A-12D are graphical illustrations of hemodynamic responses at settings with a paced A-V delay equal to the patient-specific A-V delays determined according to the methods $A\text{-}RV_{vis}$, $A\text{-}RV_{EGMV}$, $A\text{-}RV_{VCG}$, $A\text{-}RV_{aCRT}$, and $A\text{-}QRS_{onset}$;

DETAILED DESCRIPTION

Figure 1:
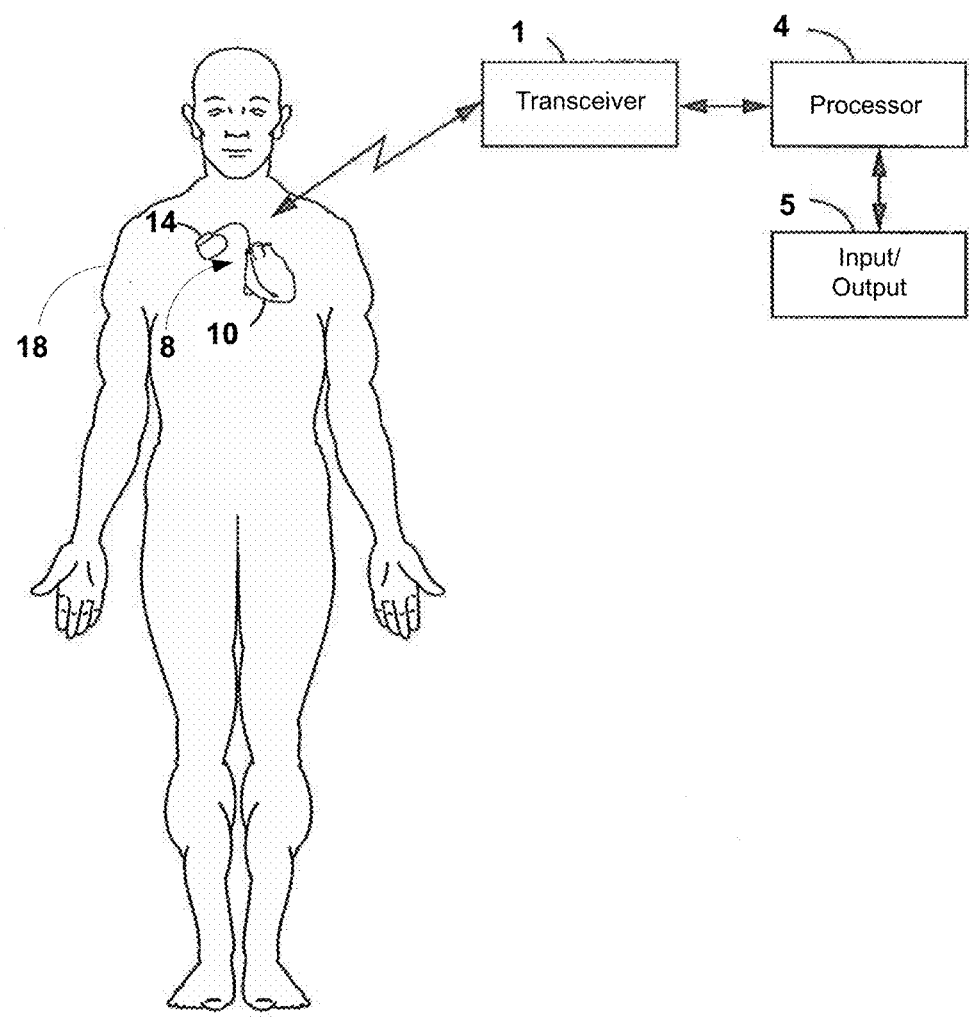
FIG. 1 is conceptual diagram illustrating an example medical device system including an implantable medical device in conjunction with a patient and one or more external devices that are coupled to the medical device.

In general, this disclosure describes example techniques related to controlling the delivery of cardiac resynchronization therapy (CRT) to a patient. One or more processors, e.g., of an implantable medical device (IMD) or an external computing device, may determine an appropriate A-V or V-V delay for the patient by delivering CRT according to varying delays and determining the value of the delay at which a change in an area or amplitude of a QRS complex occurs. This determination of the appropriate delay may occur periodically and/or in response to a change in patient state or another event. In some examples, the value of the A-V or V-V delay at which such a change occurs may approximate a patient-specific value of an A-V or V-V interval, and further may account for a latency period between delivery of CRT and activation of the paced ventricle. A memory of the implantable medical device or the external computing device may then store the determined value of the appropriate A-V or V-V delay at least until another updated value of an appropriate delay is determined.

Although some other techniques may be used to determine an appropriate A-V or V-V delay, such as different echocardiographic measures, invasive hemodynamic measures (dP/dt, stroke work), finger photoplethysmography, and peak endocardial acceleration, most such methods are time and resource consuming and subject to large measurement variability. With exception of the last technique, measurements typically are performed during in-office visits. While the majority of large clinical trials in CRT incorporated some manner of AV-delay determination, definitive data supporting their superiority over an empiric A-V delay are lacking. For example, a limitation of echocardiographic measures is that they often may be performed with the patient in the recumbent position in full rest, although such measurements may be more useful under conditions of higher physical activity. Moreover, most such techniques are time and resource consuming and subject to large measurement variability, leading many clinicians to leave CRT device settings at the nominal values ("out-of-the-box").

In some example techniques, a patient-specific A-V and/or V-V delay accurately may be determined from a vectorcardiogram. Vectorcardiography (VCG) is a three-dimensional representation of the electrical forces present in the heart and thus may provide an accurate illustration of the extent of resynchronization during fusion or biventricular (BiV) pacing. Such three-dimensional VCGs may be derived from a body-surface ECG, such as a conventional 12-lead ECG. However, it may not be practical to equip a patient with a 12-lead ECG outside of a clinic or hospital setting.

In some cases, a two-dimensional vectorloop derived from an implantable device (a "D-VCG") may approximate a VCG for some purposes. For example, a patient-specific A-V delay, which may provide a desirable improvement in hemodynamic effect may be extracted from a VCG or a D-VCG. Animal studies have shown that a body-surface VCG may be approximated by a two-dimensional VCG derived from the electrograms obtained from the intracardiac pacing electrodes (e.g., a D-VCG). Thus, it may be advantageous in some cases to provide a technique for ongoing, ambulatory determination of a patient-specific A-V and/or V-V delay based on a D-VCG derived from components of an implantable medical device, in addition to or instead of determinations made based on a three-dimensional VCG. In addition, the techniques described herein may provide more accurate pacing data for an individual patient, since average data from multiple patients is not relied upon for updating an A-V or V-V delay used in pacing, and may continuously adapt to conditions such as exercise, sleep, worsening or improving cardiac function.

In some examples, a VCG or D-VCG may represent a QRS complex that results from the delivery of CRT according to a paced A-V or V-V delay. During delivery of CRT according to the techniques described herein, one or more processors, e.g., of the implantable medical device, may determine that a current period of time has elapsed or an event indicating a change in patient status has occurred, and enter a testing phase to determine an updated A-V or V-V delay. The processing circuitry may then construct a two-dimensional D-VCG by plotting two bipolar electrograms (EGMs) of the implantable medical device against each other. For example, as described below with respect to FIG. 2, a first bipolar EGM of the D-VCG may be acquired by subtracting a unipolar EGM signal from a right ventricular (RV) ring from a unipolar EGM of a proximal (P4) electrode on the LV lead. A second bipolar lead may be acquired by subtracting a unipolar EGM signal of the same RV ring from the unipolar EGM of the distal (D1) electrode of the LV lead. Each EGM so derived may represent a QRS complex resulting from the delivery of CRT at the corresponding A-V or V-V delay. As described below, the QRS complexes represented by the EGMs so obtained may be analysed with respect to one another in one or more ways, e.g., by forming a VCG, or a D-VCG or EGMV, to determine a patient-specific A-V or V-V delay.

For example, in order to determine a patient-specific A-V delay, pacing pulses may be delivered according to a range of paced A-V delays, and a VCG or D-VCG may be derived from a patient response to each paced A-V delay. In some such examples, a minimum area or a median amplitude of a QRS-complex represented by a VCG or D-VCG may predict a patient-specific A-V delay that accurately reflects intrinsic activation of the non-paced ventricle. As observed by Prinzen et al. (see FIG. 1 of U.S. Pat. No. 9,248,294 B2 to Prinzen et al. issued Feb. 2, 2016, and assigned to the assignee of the present invention, the disclosure of which is incorporated by reference in its entirety herein), the best hemodynamic response ("$VTI_{LVOT}$") and the most physiological contraction pattern (e.g., the minimal value of septal systolic pre-stretch (SPS)+rebound stretch (SRS)) occur at AV- and VV-intervals where the three-dimensional area of the QRS-complex on the VCG loop ($QRSV_{area}$) is minimal. The minimal ($QRS_{area}$) and the QRS amplitude ($QRS_{ampl}$) closest to a value halfway between LV and a left-bundle branch block ("LBBB") have been shown to predict an AV-delay resulting in the greatest hemodynamic improvement in some patients.

In other such examples, a patient-specific A-V delay may be determined by analyzing an amplitude of a QRS complex reflected by the D-VCG during CRT delivery according to paced A-V delays of sequentially changing, e.g., increasing, duration. The longest paced A-V delay at which the $QRS_{ampl}$ of the QRS complex remains unchanged from the $QRS_{ampl}$ corresponding to one or more shorter paced A-V delays reflects the onset of intrinsic ventricular activation of the non-paced ventricle, and may correspond with an increased LV $dP/dt_{max}$. Since fusion of the activation of the paced ventricle with the intrinsic activation of the non-paced ventricle is desired, the processing circuitry selects this A-V delay for use in delivering CRT during a subsequent period of time.

In some medical devices configured to deliver CRT, the A-V delay by which CRT is delivered may be periodically adjusted to achieve more efficient physiologic pacing and improve hemodynamics of the patient. For example, adequate fusion of ventricular action results in improved patient outcomes by synchronizing the activation of the ventricles, thereby increasing the systolic pressure or the maximal rate of pressure increase (LVdP/dtmax) of the paced ventricle. Fusion pacing and biventricular pacing are described in further detail below. While the pacing stimuli may be pacing pulses or continuous time signals, the pacing stimuli are primarily referred to herein as pacing pulses for ease of description.

Fusion-based CRT (also referred to herein as fusion pacing) may be useful for restoring a depolarization sequence of a heart of a patient, which may be irregular due to ventricular dysfunction, in patients with preserved intrinsic atrial-ventricular (AV) conduction. In a fusion pacing configuration, a medical device delivers one or more fusion pacing pulses to one of the ventricles, and not the other. In particular, the medical device delivers the one or more fusion pacing pulses to a later-contracting ventricle (V2) in order to pre-excite the V2 and synchronize the depolarization of the V2 with the depolarization of the earlier contracting ventricle (V1). The ventricular activation of the V2 may "fuse" (or "merge") with the ventricular activation of the V1 that is attributable to intrinsic conduction of the heart. In this way, the intrinsic and pacing-induced excitation wave fronts may fuse together such that the depolarization of the V2 is resynchronized with the depolarization of the V1.

The medical device may be configured to deliver the fusion pacing pulse to the V2 according to a fusion pacing interval, which indicates the time relative to an atrial pace or sense event at which the fusion pacing pulse should be delivered to the V2. An atrial sense event may be, for example, a P wave of a sensed electrical cardiac signal and an atrial pacing event may be, for example, the time at which a stimulus is delivered to the atrium.

In some examples, the right ventricle (RV) may be the V1 and the left ventricle (LV) may be the V2. In other examples, the LV may be the V1 while the RV may be the V2. While the disclosure primarily refers to examples in which the first depolarizing ventricle V1 is the RV and the later depolarizing ventricle V2 is the LV, the devices, systems, techniques described herein for providing CRT may also apply to examples in which the first depolarizing ventricle V1 is the LV and the later depolarizing ventricle V2 is the RV.

In some fusion pacing techniques, a pacing pulse to the V2 ($V2_P$) is delivered upon expiration of a fusion pacing interval that is determined based on the intrinsic depolarization of the V1, which may be indicated by a sensing of ventricular activation ($V1_S$). Ventricular activation may be indicated by, for example, an R-wave of a sensed electrical cardiac signal. An example of a fusion pacing technique that times the delivery of the V2 pacing pulse ($V2_P$) to the intrinsic depolarization of the V1 is described in U.S. Pat. No. 7,181,284 to Burnes et al., which is entitled, "APPARATUS AND METHODS OF ENERGY EFFICIENT, ATRIAL-BASED BI-VENTRICULAR FUSION-PACING," and issued on Feb. 20, 2007. U.S. Pat. No. 7,181,284 to Burnes et al. is incorporated herein by reference in its entirety.

In one example disclosed by U.S. Pat. No. 7,181,284 to Burnes et al., a pacing pulse to the V2 ($V2_P$) is delivered a predetermined period of time following an atrial pace or sense event ($A_{P/S}$), where the predetermined period of time is substantially equal to the duration of time between the atrial pace or sense event ($A_{P/S}$) and a V1 sensing event ($V1_S$) of at least one prior cardiac cycle decremented by a duration of time referred to as the pre-excitation interval (PEI). Thus, one example equation that may be used to determine a fusion pacing interval ($A_{P/S}$–$V2_P$):

$$A_{P/S}-V2_P=(A_{P/S}-V1_S)-\text{PEI} \qquad \text{Equation (1)}$$

A cardiac cycle may include, for example, the time between the beginning of one heart beat to the next heartbeat. The duration of time between the atrial pace or sense event ($A_{P/S}$) and a V1 sensing event ($V1_S$) may be, for example, a measurement of intrinsic AV conduction time from an atrium to the first contracting ventricle of the heart of the patient. The PEI may indicate the amount of time with which a V2 pacing pulse precedes a V1 sensing event in order to achieve the fusing of the electromechanical performance of the V1 and V2 (e.g., the latency of activation of V2). That is, the PEI may indicate the amount of time from the delivery of the V2 pacing pulse that is required to pre-excite the V2, such that the electromechanical performance of V1 and V2 merge into a fusion event. In some examples, the PEI is automatically determined by a medical device delivering the pacing therapy, e.g., based on determined intrinsic conduction times, while in other examples, the PEI may be predetermined by a clinician. In some examples, the PEI is a programmed value (e.g., about one millisecond (ms) to about 250 ms or more, such as about 100 ms to about 200 ms, or about 10 ms to about 40 ms) or is an adaptive value, such as about 10% of a measured intrinsic A-V2 conduction interval or measured intrinsic A-A cycle length.

The magnitude of the PEI may differ based on various factors, such as the heart rate of the patient, a dynamic physiologic conduction status of the heart of the patient, which may change based upon the physiological condition of the patient (e.g., ischemia status, myocardial infarction status, and so forth), as well as factors related to the therapy system, such as the location of sensing electrodes of the leads of the therapy system, the location of the pacing electrodes of the therapy system, and internal circuitry processing delays of the medical device.

In some other example techniques for determining an appropriate A-V delay by which to deliver CRT, such as those which directly measure an A-V interval in the absence of pacing, the appropriate A-V delay may have to account for the PEI as shown above. In contrast, to determine an appropriate A-V delay according to the techniques described herein, e.g., using a D-VCG, pacing is performed and the paced A-V delay is sequentially changed, e.g., prolonged, to detect the onset of intrinsic non-paced ventricle contribution. Detection of the onset of intrinsic non-paced ventricle contribution in this manner is based on actual measured changes in activation and not on predicted values. In this manner, the techniques described herein may directly measure the moment fusion, whether LV latency is present or not. Moreover, unlike some other example techniques, the determination of an appropriate A-V delay based on a D-VCG is independent of the placement of the leads. For example, studies have shown that placement of a non-paced RV lead in the RV outflow tract (RVOT) did not affect the value of the A-V delay determined using a D-VCG. Thus, the techniques described herein for determination of an appropriate A-V delay for CRT advantageously may be more robust and less susceptible to confounding factors than other known techniques.

The techniques described herein also may be useful in the selection of appropriate locations for the pacing electrodes used to deliver CRT. During the procedure for measuring the D-VCG and optimizing the V-V and A-V intervals, it is generally preferred to pace using electrodes that are not being employed to measure a D-VCG, although other electrode configurations may be substituted. For example, if an implantable medical device includes defibrillation capabilities, one or more of the electrodes employed to measure the D-VCG may be defibrillation electrodes. In some examples, a clinician may be able to select which electrodes are employed to perform the various functions if a sufficient number of electrodes are available. For example, during initial implant of the implantable medical device, determination of an appropriate A-V delay iteratively may be performed with the relevant RV and LV electrodes located at different sites. Based upon the results, the clinician may choose a preferred set of locations for initial implant.

As the number and locations of electrodes increases, there also may be circumstances in which the selection of the electrodes to be used for pacing also may be adjustable after implant. In such cases, as with initial implant, iterative application of the methodology herein to the available pacing electrode configurations may also be performed. In such examples, a clinician may wish to review the results for the various electrode configurations available, and independently determine which configuration to employ. In other examples, however, an implantable medical device itself may periodically test the available electrode configurations, and either recommend a preferred configuration or select a preferred configuration automatically.

Figure 2:
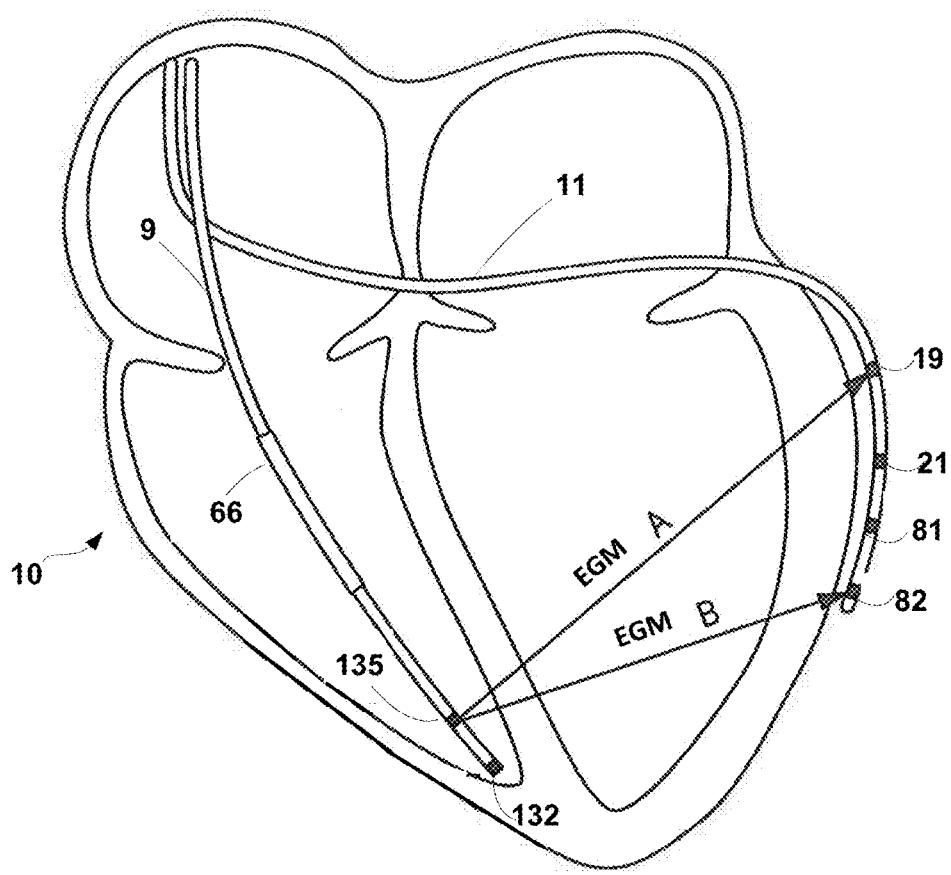
FIG. 2 is a conceptual diagram of a portion of a left ventricular lead and a right ventricular lead of in a patient's heart, illustrating electrograms that may be acquired according to some examples according to this disclosure.
Figure 3:
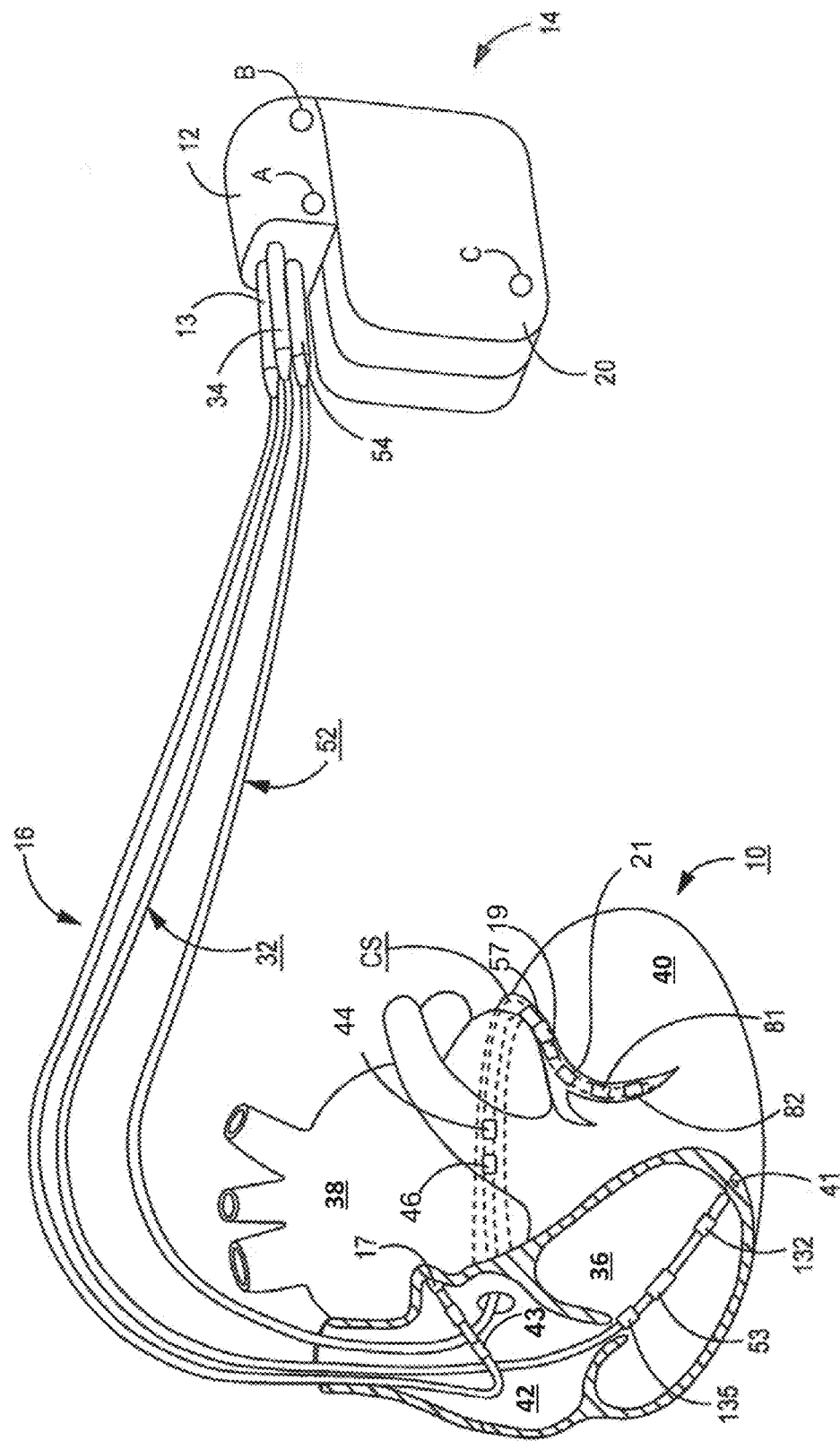
FIG. 3 is a conceptual diagram illustrating the implantable medical device of FIG. 1 and an example set of leads.
Figure 4:
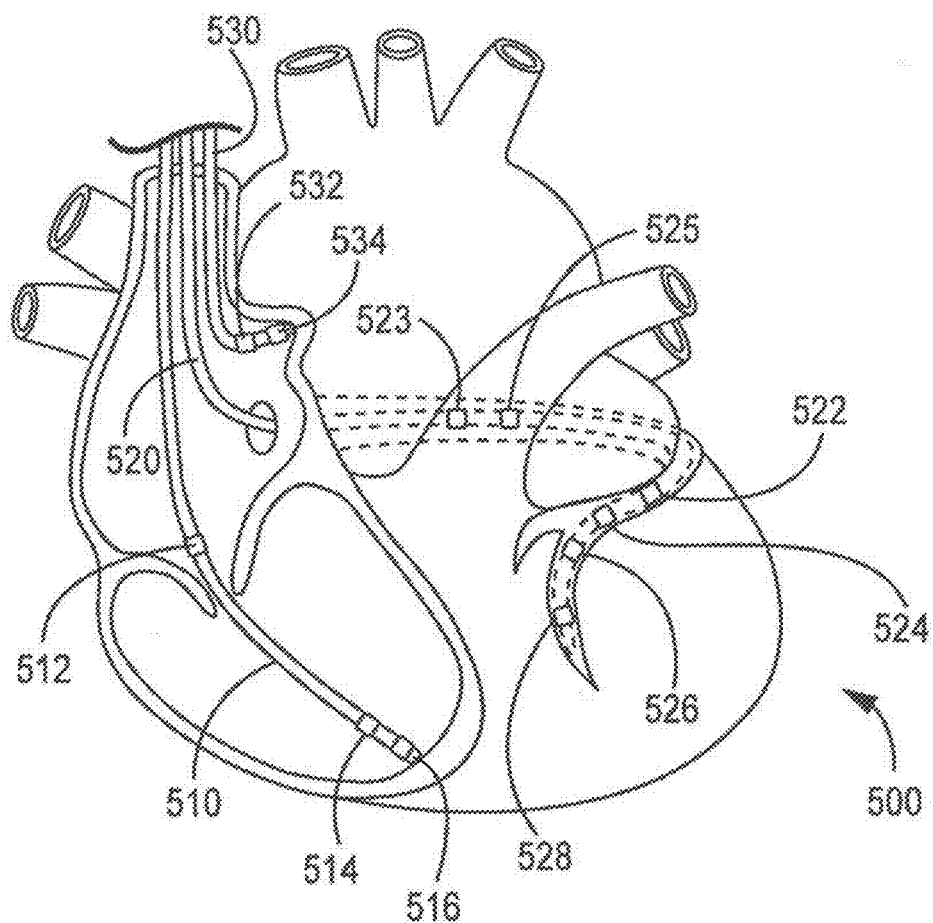
FIG. 4 is a conceptual diagram illustrating another example set of leads that may be used with the medical device system of FIG. 1.

FIG. 1 illustrates the environment of an example medical device system 8 in conjunction with patient 18, in accordance with an apparatus and method of certain examples of this invention. The invention may be used with an implantable medical device (IMD) 14, which may be a pacemaker, illustrated as implanted within patient 18. Connected to IMD 14 is are one or more leads (e.g., such as shown in FIGS. 2-4), which extend into heart 10, and which include one or more electrodes at distal ends thereof that deliver stimulus pulses and also sense intracardiac or epicardial signals. As is well known in the pacemaker art, the sense signals can be received by the pacemaker, digitized and stored in memory, for later transmission to an external device; alternately, they can be downloaded directly to an external programmer device. Likewise, one or more sensors located on a lead of IMD 14 or otherwise associated with IMD 14 can produce the signals that are to be digitized and stored. As shown, transceiver 1 may be a conventional programmer as used in the pacemaker art. The programmer, when it has received data from the pacemaker, can transfer it to a processor 4, which in turn can output data to input/output device 5, all in a well-known manner.

Figure 5:
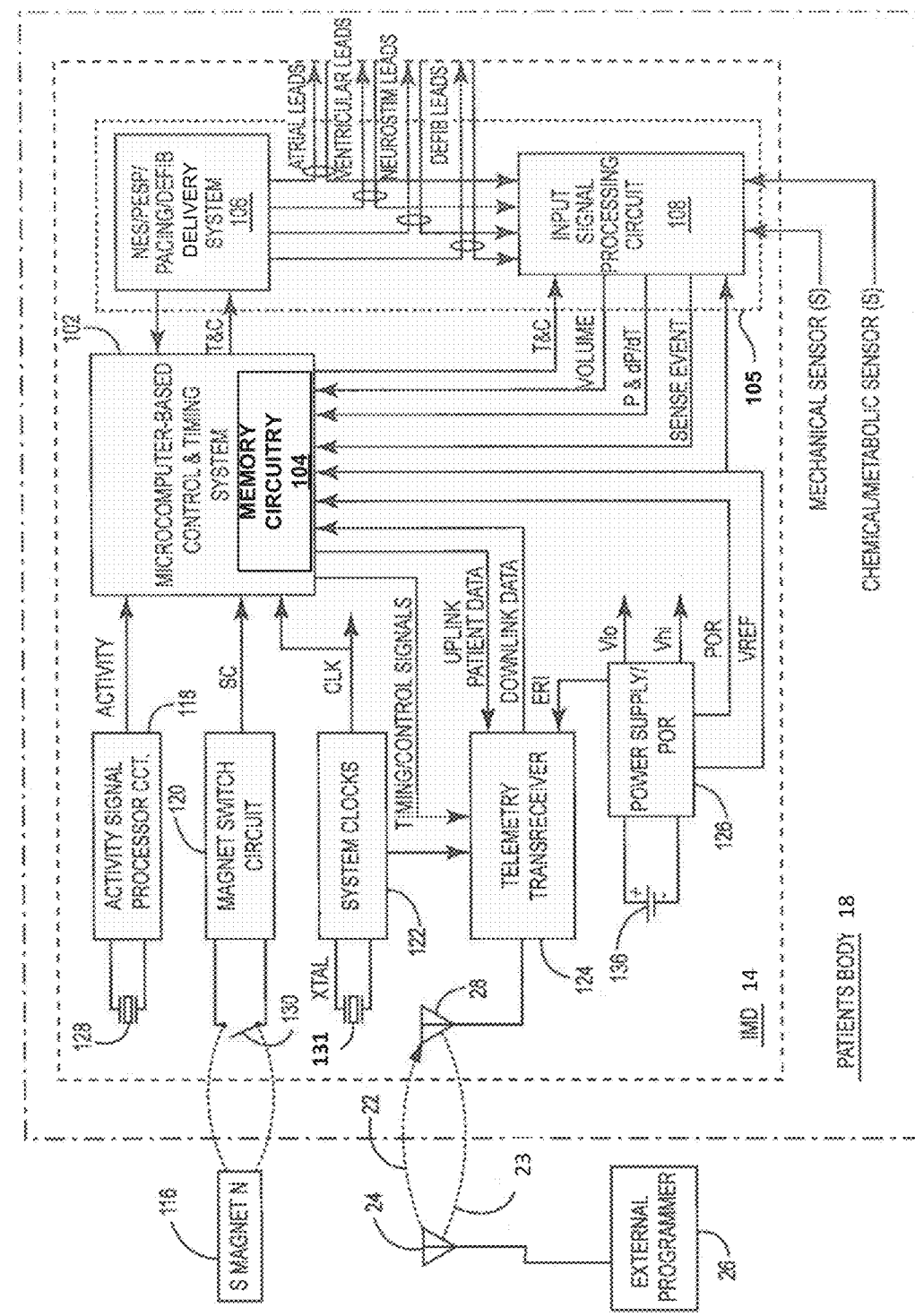
FIG. 5 is a schematic diagram depicting an example configuration of the medical device of FIG. 1.
Figure 6:
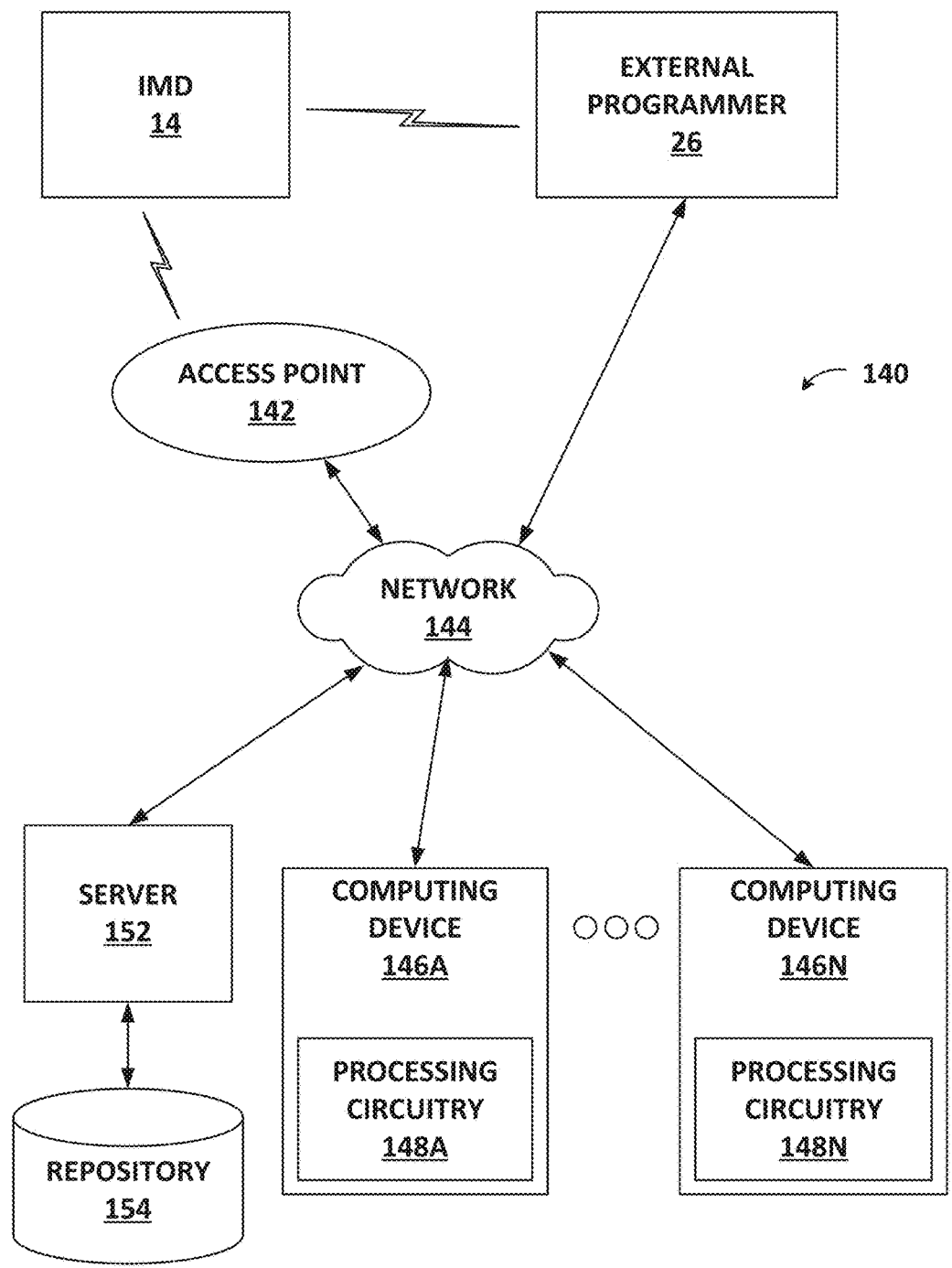
FIG. 6 is a block diagram illustrating an example system that includes the implantable medical device of FIG. 1 and one or more external devices that are coupled to the medical device via a network.

Transceiver 1, processor 4, and input/output device 5 may be embodied in a single device, e.g., external programmer 26 of FIGS. 5 and 6, or in multiple co-located or networked devices. A user, such as a physician, technician, or other clinician, may interact with external programmer 26 to communicate with IMD 14. For example, the user may interact with external programmer 26 to retrieve physiological or diagnostic information from IMD 14. A user may also interact with external programmer 26 to program IMD 14, e.g., to select values for operational parameters of the IMD. Transceiver 1 may facilitate communication with IMD 14 via wireless communication using any techniques known in the art. Examples of communication techniques may include, for example, include radiofrequency (RF) telemetry, which may be an RF link established via an antenna according to Bluetooth, WiFi, or medical implant communication service (MICS), though other techniques are also contemplated.

Medical device system 8 is an example of a medical device system that is configured to implement the example techniques described herein for controlling the delivery of CRT to heart 10 of patient 18. IMD 14 may be an implanted, multi-channel cardiac pacemaker, implantable cardioverter-defibrillator (ICD), implantable pulse generator (IPG), leadless (e.g., intracardiac) pacemaker, extravascular pacemaker and/or ICD, or other IMB or combination of IMDs for restoring A-V synchronous contractions of the atrial and ventricular chambers and simultaneous or sequential activation of the right and left ventricles.

IMD 14 is configured to provide CRT to heart 10. In some examples, as part of the CRT, IMD 14 is configured to deliver at least one of fusion pacing to heart 10 and biventricular pacing to heart 10. In some examples of fusion pacing, IMD 14 may deliver a pacing stimulus (e.g., a pacing pulse) to the left ventricle (LV) of heart 10, where the pacing stimulus is timed such that an evoked depolarization of the LV is effected in fusion with the intrinsic depolarization of the right ventricle (RV) of heart 10, resulting in a ventricular resynchronization. In this way, the pacing pulse delivered to the LV may pre-excite a conduction delayed LV and help fuse the activation of the LV with the activation of the RV from intrinsic conduction. The fusion of the depolarization of the LV and RV may result in synchronous activation and contraction of the LV with the RV. In examples described herein, the fusion pacing configuration may be referred to as "left-ventricular" pacing. However, it should be understood that a fusion pacing configuration may also include right-ventricular pacing in any of the examples described.

In some examples, when IMD 14 is in a biventricular pacing configuration, IMD 14 may deliver a pacing stimulus (e.g., a pacing pulse) to the RV and a pacing stimulus to the LV in a manner that synchronizes activation and contraction of the RV and LV, e.g., based on a selected or determined V-V delay.

In some examples, the CRT provided by IMD 14 may be useful for maintaining the cardiac rhythm in patient 18 with a conduction dysfunction, which may result when the natural electrical activation system of heart 10 is disrupted. The natural electrical activation system of a human heart 10 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of right atrium (RA). The depolarization wave is transmitted through the atrial conduction pathways of Bachmann's Bundle and the Internodal Tracts at the atrial level into the left atrium (LA) septum. When the atrial depolarization wave has reached the AV node, the atrial septum, and the furthest walls of the right and left atria, respectively, the atria may contract as a result of the electrical activation. The aggregate right atrial and left atrial depolarization wave appears as the P-wave of the PQRST complex of an electrical cardiac signal, such as a cardiac EGM or ECG. When the amplitude of the atrial depolarization wave passing between a pair of unipolar or bipolar pace/sense electrodes located on or adjacent the RA and/or LA exceeds a threshold, it is detected as a sensed P-wave. The sensed P-wave may also be referred to as an atrial sensing event, or an RA sensing event (RAS). Similarly, a P-wave sensed in the LA may be referred to as an atrial sensing event or an LA sensing event (LAS).

During or after the atrial contractions, the AV node distributes the depolarization wave inferiorly down the Bundle of His in the intraventricular septum. The depolarization wave may travel to the apical region of heart 10 and then superiorly though the Purkinje Fiber network. The aggregate right ventricular and left ventricular depolarization wave and the subsequent T-wave accompanying repolarization of the depolarized myocardium may appear as the QRST portion of the PQRST cardiac cycle complex. When the amplitude of the QRS ventricular depolarization wave passing between a bipolar or unipolar pace/sense electrode pair located on or adjacent the RV and/or LV exceeds a threshold, it is detected by IMD 14 as a sensed R-wave. The sensed R-wave may also be referred to as a ventricular sensing event, an RV sensing event (RVS), or an LV sensing event (LVS) depending upon the ventricle in or near which the electrodes, e.g., of one or more of leads, are configured to sense in a particular case.

Some patients, such as patients with congestive heart failure or cardiomyopathies, may have left ventricular dysfunction, whereby the normal electrical activation sequence through heart 10 is compromised within the LV. In a patient with left ventricular dysfunction, the normal electrical activation sequence through the heart of the patient becomes disrupted. For example, patients may experience an intra-atrial conduction defect, such as intra-atrial block. Intra-atrial block is a condition in which the atrial activation is delayed because of conduction delays between the RA to the LA.

As another example, a patient with left ventricular dysfunction may experience an interventricular conduction defect, such as left bundle branch block (LBBB) and/or right bundle branch block (RBBB). In LBBB and RBBB, the activation signals are not conducted in a normal fashion along the right or left bundle branches respectively. Thus, in patients with bundle branch block, the activation of either the RV or LV is delayed with respect to the other ventricle, causing asynchrony between the depolarization of the right and left ventricles. Ventricular asynchrony may be identified by a widened QRS complex due to the increased time for the activation to traverse the ventricular conduction paths. The asynchrony may result from conduction defects along the Bundle of His, the Right and Left Bundle Branches or at the more distal Purkinje Terminals. Typical intra-ventricular peak-to-peak asynchrony can range from about 80 milliseconds (ms) to about 200 ms or longer. However, in patients who are experiencing RBBB and LBBB, the QRS complex may be widened far beyond the normal range to a wider range, e.g., about 120 ms to about 250 ms or greater.

CRT delivered by IMD 14 may help alleviate heart failure conditions by restoring synchronous depolarization and contraction of one or more chambers of heart 10. In some cases, the fusion pacing or other CRT of heart 10 described herein enhances stroke volume of a patient by improving the synchrony with which the RV and LV depolarize and contract.

The duration of a cardiac cycle of heart 10, which includes the depolarization-repolarization sequence, may change depending on various physiological factors of patient 18, such as a heart rate. As heart rate of patient 18 changes, the timing of the delivery of a pacing pulse to the LV (LVP) during fusion pacing therapy or the timing of the delivery of pacing pulses to the RV (RVP) and LV (LVP) during biventricular pacing therapy may change. Accordingly, when IMD 14 is delivering fusion pacing to heart 10, it may be useful for IMD 14 to periodically adjust the A-V delay by which CRT is delivered, in order to maintain the delivery of the LV pacing pulse (LVP) at a time that results in a fusion of the depolarization of LV and RV. In some examples, IMD 14 may determine an updated A-V delay for fusion pacing at predetermined intervals, such as once per minute, once per hour, or semi-continuously, although other intervals may also be used. Additionally or alternatively, IMD 14 may determine an updated A-V delay for fusion pacing based on a detected change in heart rate that exceeds a threshold value, which may be indicative of the patient's sleep or exercise state. In both such examples, the updated A-V delay may be determined based on a D-VCG derived from unipolar electrograms recorded from the unpaced electrodes, e.g., of one or more leads coupled to IMD 14, as described above.

In some examples, IMD 14 also provides defibrillation therapy and/or cardioversion therapy. IMD 14 may detect arrhythmia of heart 10, such as fibrillation of the ventricles, and deliver defibrillation therapy to heart 10 in the form of electrical shocks. In some examples, IMD 14 is programmed to deliver a progression of therapies, e.g., shocks with increasing energy levels, until a fibrillation of heart 10 is stopped. In examples in which IMD 14 provides defibrillation therapy and/or cardioversion therapy, IMD 14 may detect fibrillation by employing any one or more fibrillation detection techniques known in the art.

FIG. 2 is a conceptual diagram of a portion of left ventricular lead 11 and right ventricular lead 9 that may be coupled to IMD 14 of FIG. 1 and positioned in heart 10. In this example, the available signals from unpaced electrodes include the unipolar EGMs of the RV ring electrode 135, proximal (P4) electrode 19 on the LV lead 11, and distal (D1) electrode 82 on the LV lead 11. The other electrode for each of these unipolar EGMs may be a can or housing electrode 20 (FIG. 3) of IMD 14, or a defibrillation coil electrode, e.g., electrode 66 on RV lead 9.

One or more processors, e.g., of IMD 14 and/or processor 4 (FIG. 1) may calculate bipolar EGM A by subtracting the unipolar EGM signal from electrode 135 of lead 9 from the unipolar EGM of electrode 19 on lead 11, and bipolar EGM B by subtracting the unipolar EGM signal of electrode 135 of lead 9 from the unipolar EGM of electrode 82 of LV lead 11. The one or more processors may construct a two-dimensional D-VCG by plotting EGM A and EGM B against each other. In this example, electrodes 21 and 81 are the pacing electrodes.

In experiments conducted by the inventors, and described in greater detail below, the D-VCG was analyzed using software programmed in MATLAB R2010b (MathWorks, Natick, Mass.), and could be analyzed by any like software executed by the one or more processors, e.g., of IMD 14 and/or processor 4. In such examples, the magnitude and direction of the maximum QRS vector in space may be expressed as amplitude and angle. Although the techniques described herein are primarily described as pertaining to a two-dimensional D-VCG, a three-dimensional VCG may be used additionally or alternatively. For example, a three-dimensional VCG may be derived from an ECG during a clinician's visit as a supplement to or confirmation of the A-V and/or V-V delay values obtained using a two-dimensional D-VCG. In either case, an area of a QRS loop ("$QRS_{area}$") representative of a QRS complex may additionally or alternatively be calculated.

The $QRS_{ampl}$ was defined negative when the vector was directed towards the back (negative azimuth) or, in the case of the D-VCG, towards RV ring electrode 135. In the example of a three-dimensional VCG, the area of the QRS loop may be calculated from the area under the curve from beginning to end of the QRS complex in the three orthonormal axes X, Y, and Z, using the following equation:

$$QRS_{area}=(QRS_{area,x2}+QRS_{area,y2}+QRS_{area,z2})^{1/2} \quad \text{Equation (2)}$$

Because in D-VCG only two dimensions may be represented, an angle expressed in the plane formed by the unipolar EGMs and an area calculation using the following equation:

$$QRS_{area}=(QRS_{area,A2}+QRS_{area,B2})^{1/2} \quad \text{Equation (3)}$$

According to the techniques described herein, one or more processors may determine an A-V and/or V-V delay for delivery of biventricular pacing or fusion pacing based on identification of a target value of QRS amplitude and/or QRS area. For example, the one or more processors may sequentially test a plurality of values of the delay, and identify a value of the delay corresponding to a target change in QRS amplitude or QRS area, or a minimal value of QRS area. Where sequentially longer delays are tested, the target change may be a decrease, and the identified value may be the longest value of the delay prior to the decrease, or the shorter of the adjacent values at which the decrease occurred. For purpose of the invention, adjustment of A-V delays and V-V delays can be accomplished by either defining two A-V delays (e.g. A-RV and A-LV) or by defining one A-V delay and a V-V delay. Hereinafter, adjustment of A-V and V-V delays should be understood to include either approach.

The techniques described herein may be performed with an IMD operating in either a biventricular or fusion CRT mode. In the case of left-ventricular fusion pacing, the one or more processors may measure the RA to RV conduction time, rather than control it by means of an RA-RV pacing interval as would be the case for biventricular pacing. The measured RA-RV interval would be used to allow the device to sequentially scan through available A-LV intervals around the measured RA-RV interval.

FIG. 3 is a conceptual diagram illustrating IMD 14 and leads 16, 32, and 52 of one example configuration of medical device system 8. Endocardial leads 16, 32, and 52 connect IMD 14 with RA 42, RV 36 and LV 40, respectively. Each lead includes electrical conductors and pace/sense electrodes. A remote indifferent can electrode 20 may be formed as part of the outer surface of the housing of the IMD 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover, other leads and pace/sense electrodes may be used instead of the depicted leads and pace/sense electrodes that are adapted to be placed at electrode sites on or in or relative to RA 42, LA 38, RV 36, and LV 40.

The endocardial RV lead 32 is passed through a vein into RA 42 of the heart 10, and the distal end of the RV lead 32 is attached to the RV wall by an attachment mechanism 41. The endocardial RV lead 32 is formed with an in-line connector 34 fitting into a bipolar bore of IPG connector block 12 that is coupled to electrically insulated conductors within the lead body and connected with the electrodes thereon. In the case in which the electrode configuration of FIG. 2 is employed, lead 32 would carry electrodes 135 and 132. Additional electrodes may be provided as discussed below in conjunction with FIG. 4.

Delivery of atrial pacing pulses and sensing of atrial sense events is effected using lead 16, by means of the distal tip RA pace/sense electrode 17 and proximal ring RA pace/sense electrode 43, wherein the proximal ring RA pace/sense electrode 43 functions as an indifferent electrode (IND_RA). The endocardial RV lead 16 is formed with an in-line connector 13 fitting into a bipolar bore of IPG connector block 12 that is coupled to electrically insulated conductors within the lead body and connected with the electrodes thereon.

Lead 52 may be a multi-electrode endocardial lead passed through the right atrium, through the coronary sinus and into the great cardiac vein. In the case in which the electrode configuration of FIG. 2 of U.S. Pat. No. 9,248,294 to Prinzen et al. is employed to determine a D-VCG, lead 52 would carry electrodes 19, 21, 81, 82, and, if present, electrodes 44 and 46 (all illustrated in FIG. 2 of U.S. Pat. No. 9,248,294). Additional electrodes may be provided as discussed below in conjunction with FIG. 4. The endocardial RV lead 52 is formed with an in-line connector 54 fitting into a bipolar bore of IPG connector block 12 that is coupled to electrically insulated conductors within the lead body and connected with the electrodes thereon.

Also depicted in FIG. 3 is an optional RV sensor 53 and an optional LV sensor 57 which each may comprise one or more of a variety of sensors as is known in the art. Preferably RV sensors 53 and/or 57, if present, comprise absolute pressure sensors, but other pressure sensors may be utilized. Additionally or alternatively, sensors 53 and 57 may comprise accelerometers, impedance electrodes, saturated oxygen sensors, pH sensors, or the like. Of course, such sensors must be rendered biocompatible and reliable for long-term use. In addition, one or more sensors may be disposed in or on the housing 20 of IMD 14 such as sensors A, B, or C depicted in FIG. 3.

In some examples, housing 20 may enclose therapy delivery circuitry that generates cardiac pacing pulses and defibrillation or cardioversion shocks, as well as sensing circuitry for monitoring the patient's heart rhythm. In some examples, leads 16, 32, and 52 may also include elongated electrodes, e.g., electrode 66 (FIG. 2), each of which may take the form of a coil. IMD 14 may deliver defibrillation pulses to heart 10 via any combination of elongated electrodes and housing electrode 20. Elongated electrodes may also be used to deliver cardioversion pulses to heart 10. Additionally, as described above, such elongated electrodes may be used as an indifferent electrode in a unipolar sensing or pacing configuration. The elongated electrodes may be fabricated from any suitable electrically conductive material, such as, but not limited to, platinum, platinum alloy or other materials known to be usable in implantable defibrillation electrodes.

The configuration of therapy system 8 illustrated in FIGS. 1-3 is one example, and is not intended to be limiting. In other examples, a therapy system may include extravascular electrodes, such as subcutaneous electrodes, substernal electrodes, epicardial electrodes, and/or patch electrodes, instead of or in addition to the electrodes of transvenous leads 16, 32, and 52 illustrated in FIG. 3. Further, IMD 14 need not be implanted within patient 18. In examples in which IMD 14 is not implanted in patient 18, IMD 14 may deliver defibrillation pulses, pacing pulses, and other therapies to heart 10 via percutaneous leads that extend through the skin of patient 18 to a variety of positions within or outside of heart 10.

In other examples of medical device systems that provide electrical stimulation therapy to heart 10, a therapy system may include any suitable number of leads coupled to IMD 14, and each of the leads may extend to any location within or proximate to heart 10. For example, a therapy system may include a dual chamber device rather than a three-chamber device as shown in FIG. 3. In one example of a dual chamber configuration, IMD 14 is electrically connected to a single lead that includes stimulation and sense electrodes within LV 40 as well as sense and/or stimulation electrodes within RA 42. In another example of a dual chamber configuration, IMD 14 is connected to two leads that extend into a respective one of RA 42 and LV 40.

In some examples, a medical device system includes one or more leadless (e.g., intracardiac) pacing devices (LPDs) instead of, or in addition to, an IMD coupled to leads that extend to heart 10, like IMD 14. The LPDs may include therapy delivery and processing circuitry within a housing configured for implantation on or within one of the chambers of heart 10. In such systems, the one or more pacing devices, which may include one or more LPDs and/or an IMD coupled to one or more leads, may communicate to coordinate sensing and pacing in various chambers of heart 10 to provide CRT according to the techniques described herein. Processing circuitry and memory of one or more of the pacing devices, and/or another implanted or external medical device, may provide the functionality for controlling delivery of CRT ascribed to processing circuitry and memory 104 of IMD 14 herein.

In some examples, one or more LPDs on or within one or both of the RV 36 and LV 40 may act as slave devices to provide biventricular or fusion CRT. The master device that controls the timing of the delivery of pacing by the LPD(s) may be a leaded pacemaker or ICD as illustrated in FIG. 3, an extravascular ICD, or an implantable cardiac monitor, such as the REVEAL™ or LINQ™ insertable cardiac monitors commercially available from Medtronic, plc of Dublin, Ireland. The master device may include or be coupled to electrodes, and configured to acquire one or more electrograms and determine CRT parameters for the delivery of pacing by the LPD(s) based on the electrograms according to the techniques described herein.

FIG. 4 is a conceptual diagram of a heart 500 and an alternative arrangement of leads, that may be coupled to an implantable medical device, such as IMD 14, for acquiring electrograms and determining CRT parameters according to the techniques described here. Right ventricular lead 510 carries electrodes 512, 514 and 516. Left ventricular lead 520 carries electrodes 522, 523, 524, 525, and 526. In conjunction with measurement along the X axis, e.g., for a three-dimensional VCG, electrodes 514 and 522 may be employed. In conjunction with measurement along the Y axis, electrodes 512 and 528 may be employed. In conjunction with measurement along the Z axis, if employed, electrodes 512 and 522, 523 or 525 may be used. Sensing and pacing of the left ventricle may be performed using electrodes 524 and 526, which may take the form of a closely spaced bipolar pair. Sensing and pacing of the right ventricle may be performed using electrode 516 in conjunction with a remote indifferent electrode or in conjunction with an additional electrode on lead 510. Atrial pacing and sensing are done using electrodes 532 and 534 on lead 530, which may take the form of a closely spaced bipolar pair.

Other pacing and sensing configurations can be used to implement the techniques described herein. One or more examples are disclosed in patent application Ser. No. 14/173,288 filed on Feb. 5, 2014, entitled "SYSTEMS AND METHODS FOR LEADLESS CARDIAC RESYNCHRONIZATION THERAPY" and assigned to the assignee of the present disclosure, the disclosure of which is incorporated by reference in its entirety herein. In some examples, an implantable medical device can be implanted substernally/retrosternally, as described in U.S. patent application Ser. No. 61/819,946, entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE" filed May 6, 2013, incorporated by reference in its entirety. Example LPDs that may deliver pacing according to the techniques described herein, e.g., as a slave device, are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665, 492 to Bonner et al. and U.S. patent Ser. No. 13/665,601 to Bonner et al. are both incorporated herein by reference in their entireties.

One or more examples relate to a leadless pacing device (LPD) placed in the left ventricle and controlled by a subcutaneous pacing device. One or more examples involve the LPD being implanted within a chamber of the heart or substernally/retrosternally, as described in U.S. provisional patent application Ser. No. 61/819,946 filed May 6, 2013 and entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE", incorporated by reference in its entirety, U.S. provisional patent application Ser. No. 61/820,024 filed May 6, 2013 and entitled "ANCHORING AN IMPLANTABLE MEDICAL DEVICE WITHIN A SUBSTERNAL SPACE, and U.S. provisional patent application Ser. No. 61/820,014 filed May 6, 2013 and entitled "SYSTEMS AND METHODS FOR IMPLANTING A MEDICAL ELECTRICAL LEAD WITHIN A SUBSTERNAL SPACE", all of which are incorporated by reference herein. Communication between an LPD and a subcutaneous implantable cardioverter defibrillator (SICD), e.g., a master device, is described in U.S. patent application Ser. No. 13/756,085, filed on Jan. 31, 2013, incorporated herein in its entirety.

FIG. 5 is a schematic diagram depicting an example configuration of IMD 14, which may provide delivery of a therapy or physiologic input signal processing. In the illustrated example, IMD 14 includes a system architecture that is constructed about a microcomputer-based control and timing system 102 that may vary in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. In some examples, such firmware and software may be modified in situ (e.g., in vivo), and the operational characteristics may be adapted for a particular situation or patient. A physician or clinician may change one or more parameters that will cause a change in the detection or response of such algorithms. Discrete values may be changed such that a desired software routine is advantageously altered, although sometimes an entirely new set of operating software may be substituted for an existing set of operating software by any suitable means known. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor control and timing system 102 can be accomplished with dedicated circuit hardware or state machine logic rather than a programmed microcomputer.

IMD 14 also may include input signal processing circuitry 108 for receiving signals from one or more sensors associated with IMD 14, such as mechanical, chemical, or metabolic sensors. In some examples, input signal processing circuitry may be configured to process blood pressure and volumetric signals output by such sensors. Input signal processing circuitry also may receive input from the leads of IMD 14, such as leads 16, 32, 52, and any additional leads optionally connected to IMD 14, such as one or more defibrillation leads. As further illustrated in FIG. 5, a set of lead connections are depicted for making electrical connections between the circuitry of therapy delivery system 106 and input signal processing circuit 108, and the leads connected to IMD 14.

IMD 14 also may include patient interface circuitry 105 for receiving signals from sensors and pace/sense electrodes located at specific sites of the patient's heart chambers and/or delivering stimulation to derive heart failure parameters or a pacing therapy to the heart chambers. Patient interface circuitry 105 therefore comprises a therapy delivery system 106 optionally including pacing and other stimulation therapies and a physiologic input signal processing circuit 108 for processing the blood pressure and volumetric signals output by sensors. For purposes of illustration of the possible uses of these embodiments of the invention, a set of lead connections are depicted for making electrical connections between the therapy delivery system 106 and the input signal processing circuit 108 and sets of pace/sense electrodes located in operative relation to the RA, LA, RV and LV.

IMD 14 also may include at least one electrical signal amplifier circuit for amplifying, processing, and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave, R-wave, or T-wave respectively and providing an ASENSE, VSENSE or TSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in any suitable manner. In addition, the input signal processing circuit 108 includes at least one physiologic sensor signal-processing channel for sensing and processing a sensor derived signal from a physiologic sensor located in relation to a heart chamber or elsewhere in the body.

Telemetry transceiver 124 receives and transmits signals 22 and 23 to and from an external programmer 26 via antennas 24 and 28. Programming information regarding device settings, including software for use by control and timing system 102 may be received from the external programmer 26. The information received may include portions of the stored programming information embodying the QRS area or QRS amplitude calculation and CRT parameter determination methodology discussed herein, as well as control parameters for controlling general device operation by any suitable means known. The results of analysis of the D-VCG according to the techniques described herein, e.g., the D-VCG parameters and determined A-V or V-V delays, may correspondingly be transmitted to the external programmer 26 for use by a clinician.

Power is typically provided by a battery 136 and a regulated power supply 126. Timing is controlled by a system clock using crystal oscillator 131. An externally applied magnet 116 may be used in conjunction with reed switch 130 and associated circuitry 120 to enable receipt of near-field telemetry and/or to temporarily alter the operation of the device as known to the art.

An activity sensor 128 and associated circuitry 118 may be employed to provide a signal to processor 102 allowing it to regulate pacing rate as a function of detected physical activity. Other mechanical or chemical sensors, e.g. sensors 53 and 57 as discussed above in conjunction with FIG. 3 may also be employed.

In some examples, one or more mechanical sensors of IMD 14 may include one or more accelerometers. In some examples, such accelerometers may comprise one or more three-axis accelerometers. Signals generated by accelerometers may be indicative of, for example, gross body movement of patient 18, such as a patient posture or activity level. Regardless of the configuration of accelerometers, input signal processing circuit 108 may determine patient parameter values based on the signals obtained therefrom. Accelerometers of IMD 14 may produce and provide signals to input signal processing circuit 108 for a determination as to the posture and activity level of patient 18 at a given time. Input signal processing circuit 108 may then use the determined posture and activity level to further determine whether patient 18 is awake or asleep, and, if patient 18 is determined to be awake, to further determine whether patient 18 is at rest, sleeping, or exercising. As described below with respect to FIG. 12, the rest, sleep, and exercise states of patient 18 determined by input signal processing circuit 106 may cause control and timing system 102 to determine an updated value of an A-V or V-V delay of patient 18 in addition to updated values determined based on the expiration of a predetermined period of time.

In examples in which IMD 14 delivers a pacing pulse according to an A-V or V-V delay determined by control and timing system 102, therapy delivery system 106 may include a timer for determining that a period of time corresponding to the A-V or V-V delay has elapsed since the delivery of the immediately preceding pacing stimulus or intrinsic depolarization. Upon expiration of the particular timer, control and timing system 102 may control therapy delivery system 106 to deliver a pacing stimulus, according to a fusion or biventricular pacing configuration, to heart 10. For example, control and timing system 102 may generate a trigger signal that triggers the output of a pacing pulse by therapy delivery system 106.

FIG. 6 is a block diagram illustrating a system 140 that includes a server 152, a repository 154, and one or more computing devices 146A-146N that are coupled to IMD 14 and external programmer 26 shown in FIG. 1 via a network 144, according to one example. In this example, IMD 14 uses telemetry transceiver 124 (FIG. 5) to communicate with external programmer 26 via a first wireless connection, and to communicate with an access point 142 via a second wireless connection. In the example of FIG. 6, access point 142, external programmer 26, server 152, and computing devices 146A-146N are interconnected, and able to communicate with each other, through network 144. In some cases, one or more of access point 142, external programmer 26, server 152, and computing devices 146A-146N may be coupled to network 144 through one or more wireless connections. IMD 14, external programmer 26, server 152, and computing devices 146A-146N may each comprise one or more processing circuitries, such as one or more microprocessors, DSPs, ASICs, FPGAs, programmable logic circuitry, or the like, that may perform various functions and operations, such as those described herein. For example, computing devices 146A-146N may include respective processing circuitries 148A-148N, as shown in FIG. 6.

Access point 142 may comprise a device that connects to network 144 via any of a variety of connections, such as telephone dial-up, digital subscriber line (DSL), or cable modem connections. In other examples, access point 142 may be coupled to network 144 through different forms of connections, including wired or wireless connections. In some examples, access point 142 may communicate with external programmer 26 and/or IMD 14. Access point 142 may be co-located with patient 14 (e.g., within the same room or within the same site as patient 14) or may be remotely located from patient 14. For example, access point 142 may be a home monitor that is located in the patient's home or is portable for carrying with patient 14.

During operation, IMD 14 may collect, measure, and store various forms of diagnostic data. For example, as described previously, IMD 14 may collect ECG and/or EGM signals, and determine different CRT configurations and A-V and/or V-V delays. In certain cases, IMD 14 may directly analyze collected diagnostic data and generate any corresponding reports or alerts. In some cases, however, IMD 14 may send diagnostic data to external programmer 26, access point 142, and/or server 152, either wirelessly or via access point 142 and network 110, for remote processing and analysis.

In one example, server 152 may comprise a secure storage site for information that has been collected from IMD 14 and/or external programmer 26. In this example, network 144 may comprise an Internet network; and trained professionals, such as clinicians, may use computing devices 146A-146N to securely access stored data on server 152. For example, the trained professionals may need to enter usernames and passwords to access the stored information on server 152. In one embodiment, server 152 may be a CareLink server provided by Medtronic, Inc., of Minneapolis, Minn.

In some examples, processing circuitry and memory of one or more of access point 142, server 112, or computing devices 114, e.g., processing circuitry 118 and memory of server 112, may be configured to provide some or all of the functionality ascribed to control and timing system 102 and memory circuitry 104 of IMD 14. For example, such processors may be configured to derive a D-VCG or VCG from electrograms received from IMD 14, and determine CRT parameters, such as A-V and V-V delays, using any of the techniques described herein. Such processors may provide the determined parameter values to IMD 14 to control the CRT automatically, or upon approval by a clinician.

Experimental Results

For a classical VCG, ideally a perfect three-dimensional orientation of the electrodes would be desirable. However, in case of implanted pacemaker leads this is hard to achieve. Therefore, the experiments conducted by the inventors investigated the prediction of the optimal A-V and V-V delays with different configurations of electrodes.

To this purpose an extensive optimization protocol was performed using different combinations of A-RV and A-LV delays. These different A-V delays also provided variable V-V delays. Additionally, an example of such a configuration may be seen with respect to the above-referenced and incorporated U.S. Pat. No. 9,248,294 B2 to Prinzen et al.

Approximately 30-50% of patients do not experience a significant effect from CRT. A portion of patients who do not experience significant effect or non-response to CRT can be attributed to suboptimal atrioventricular (AV) timing. Some research has indicated that the largest benefit of CRT is achieved by using LV fusion pacing by programming an A-LV delay equal to the sensed or paced A-RV delay. By doing so, wavefronts originating from the LV pacing site and the right bundle branch optimally collide. In experiments, the inventors explored the possibility for patient-specific device optimization using data derived from the implanted leads, resulting in a D-VCG.

During CRT device implant procedures of 28 patients, haemodynamic measurements and 12-lead ECG recordings were performed during various AV-delays. In addition, unipolar electrograms were recorded from the implanted electrodes. Optimal haemodynamic response was defined as either the largest increase in LV systolic pressure ($LVP_{syst}$) or the largest increase in the maximal rate of LV pressure rise (LV $dP/dt_{max}$). From experimental data, it was determined that good agreement existed between the surface VCG and D-VCG derived QRS area (R=0.74) and $QRS_{AMPL}$ (R=0.80). VCG and D-VCG derived QRS area were able to predict the A-V delay resulting in highest LV systolic pressure with reasonable accuracy. However, prediction of the A-V delay resulting in highest LV $dP/dt_{max}$ was poor, because in approximately one third of patients highest LVdP/dtmax occurred at short A-V delays. The longest A-V delay showing an unaltered QRS amplitude as compared to LV-only pacing with a short A-V delay positively corresponded to the onset of contribution of ventricular activation.

The data established that QRS area derived from the VCG or D-VCG, can predict the A-V delay resulting in highest LV systolic pressure with reasonable accuracy, but not the A-V delay with the highest LV $dP/dt_{max}$. Furthermore, the onset of contribution of the intrinsic right ventricular activation can be determined using the VCG or D-VCG.

In CRT, the time-delay between activation of the right atrium and stimulation of one or both of the ventricles (A-V delay) determines the LV filling characteristics that contribute to stroke volume and cardiac output. In addition, A-V delay has impact on the amount of fusion of intrinsic conduction with paced activation waves. Multiple techniques have been used for optimization of the A-V delay, such as different echocardiographic measures, invasive haemodynamic measures (dP/dt, stroke work), finger photoplethysmography and peak endocardial acceleration. With exception of the last technique, measurements typically are performed during in-office visits. While the majority of large clinical trials in CRT incorporated some manner of A-V delay optimization, definitive data supporting their superiority over an empiric AV-delay are lacking. Moreover, most methods are time and resource consuming and subject to large measurement variability. Therefore, many clinicians leave CRT device settings at the nominal values ("out-of-the-box").

While a single A-V delay optimization is probably valuable, regular optimization, preferably in an automated fashion, may be more desirable. To this purpose, algorithms have been developed that have been implemented in implantable medical devices. Algorithms can be based on parameters measured during intrinsic activation. Parameters employed in these algorithms can be based on averaged data from a group of patients. Algorithms that employ data that is averaged for a group of patients neglects individual differences that may occur during intrinsic conduction as well as during pacing. The electrogram-based adaptivCRT™ algorithm employed in implantable medical devices, (e.g. CRT devices such as pacemakers or ICDs) commercially available from Medtronic, is the only method that provides an almost continuous automatic optimization and enables both LV pacing and BiV pacing. In the case of LV pacing, the A-LV delay is set to the onset of contribution of right ventricular activation because optimal fusion between the intrinsic activation wave and the activation wave originating from the pacing site lead to the largest haemodynamic improvement.

In their study, the inventors explored the possibility of using data derived from the implanted leads during ventricular pacing for patient-specific device optimization since previous studies from indicated that the QRS vector on the VCG reflects the degree of ventricular resynchronization during various A-V delays. Vectorcardiography is a three-dimensional representation of the electrical forces present in the heart and might thus provide a valuable description of the amount of resynchronization during LV or BiV pacing. Experimentation showed that the minimal QRS area ($QRS_{area}$) and the QRS amplitude ($QRS_{AMPL}$) closest to a value halfway between LV pacing and LBBB predicted the A-V delay settings resulting in best haemodynamic improvement in patients. In addition, in a previous animal study, body surface VCG could be extended to a VCG derived from the electrograms obtained from the intracardiac pacing electrodes (D-VCG).

Further experimentation investigated 1) whether D-VCG derived $QRS_{area}$ can be used to determine the A-V delay that provides the best hemodynamic effect and 2) how the patient-specific onset of intrinsic activation of the right ventricular can be extracted from the VCG.

The study population consisted of 28 consecutive patients referred for CRT implantation with a class I indication according to the ESC guidelines (New York Heart Association class II, III or ambulatory IV despite adequate medical treatment, in sinus rhythm, LVEF≤35% and QRS duration >120 ms with LBBB morphology). All patients were prospectively enrolled in this multicentre study. Patients presenting with ≥4 premature ventricular complexes (PVCs) on the 12-lead ECG and with moderate to severe aortic valve stenosis were excluded. In addition, all participants had to be between the age of 18 and 80 years old and needed to be capable of giving informed consent.

Standard digital 12-lead ECGs were recorded throughout the entire procedure. All participants underwent routine CRT-defibrillator implantation; all with a quadripolar LV lead. Exemplary quadripolar leads include the ATTAIN® PERFORMA™ available from Medtronic, ACUITY™ available from Boston Scientific, the Quartet™ Model 1458Q, available from St. Jude Medical, St. Paul, USA and which was used in the study. After implantation of all leads, the pressure wire was introduced via the femoral artery into the LV cavity and the pacing protocol (described below) was performed. Once the pacing protocol was completed, the leads were connected to the CRT device and the procedure was completed.

The acute haemodynamic response to CRT was assessed by invasive LV pressure measurements. From the LV pressure measurements, the systolic LV pressure ($LVP_{syst}$) and the rate of LV pressure rise (LV dP/dt) curves were determined. The $LVP_{syst}$ and maximum LV dP/dt (LV $dP/dt_{max}$) were determined per heart beat and averaged for the complete measurement period. The LV pressure measurements were performed with a 0.014 inch pressure sensor tipped transluminal guidewire (St. Jude Medical Systems AB. PressureWire, Certus™, RADI, ST. JUDE MEDICAL). Ventricular pacing measurements were alternated by baseline measurements (AAI pacing). After each transition, at least 10 seconds were used to let the pressure stabilize after which the LV pressure was measured for at least 10 seconds without any premature ventricular contractions. In order to identify the A-V delay with the largest increase in LV $dP/dt_{max}$ or $LVP_{syst}$ a parabola was fitted to the data.

BiV and LV-only pacing at different A-V delays were performed during atrial overdrive pacing (i.e. 10 bpm above intrinsic heart rate). Programmed A-V delays increased from a very short A-V delay (between 30 and 50 ms) to an A-V delay where the paced-ECG almost resembled the intrinsic ECG (pseudofusion), in steps of 30 ms. Before and after each ventricular pace setting, AAI pacing at the same heart rate was used as baseline.

12-lead ECG recordings were made at a sampling frequency of at least 1000 Hz for at least 10 seconds. From these 12-lead ECGs, three-dimensional VCGs were constructed using the Kors matrix. Two-dimensional D-VCGs were also constructed by plotting two bipolar EGMS (e.g., A and B illustrated in FIG. 2) against each other. $QRS_{area}$ and $QRS_{AMPL}$ were calculated from the VCGs and D-VCGs as described above with respect to FIG. 2.

Figure 7A:
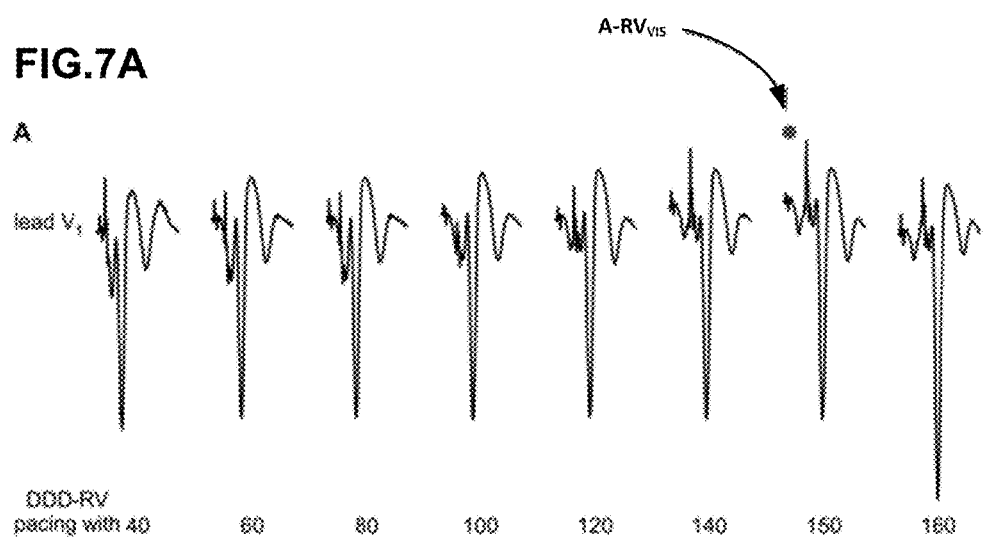
FIGS. 7A-7C are graphical illustrations of detection of activation of a right ventricle during RV-only pacing at different AV-delays using different methods.
Figure 7B:
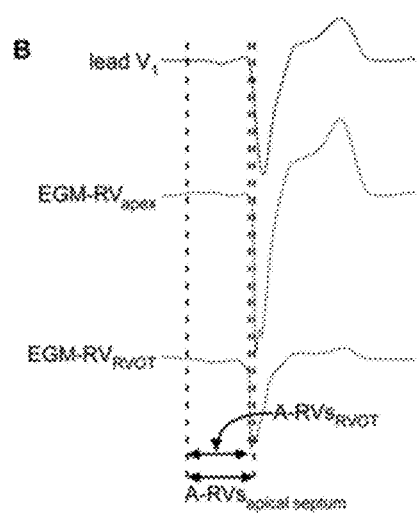
Figure 7C:
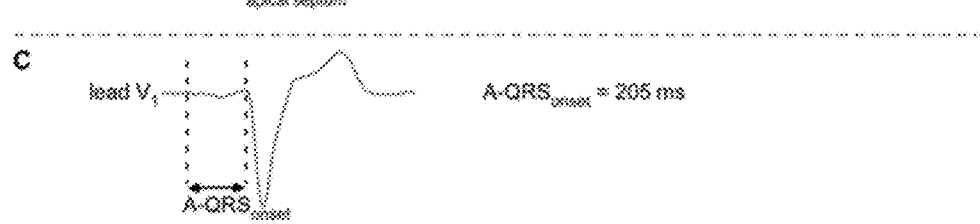

In order to obtain fusion of LV-only pacing with intrinsic right ventricular activation, it is important to determine the exact onset of contribution of intrinsic right ventricular activation. The onset in each individual patient was determined visually during RV-only pacing at different A-V delays. The A-V delay at which the shape of the QRS complex of the 12-lead ECG changed, indicating contribution of intrinsic activation of the RV, is the delay between atrial and RV activation ($A-RV_{vis}$; FIG. 7A). The adaptivCRT™ algorithm uses a formula that estimates the A-RV delay as the onset of contribution of intrinsic right ventricular activation ($A-RV_{aCRT}$): the delay between atrial sensing or pacing and RV sensing (A-RVsense) is pre-empted by 40 ms or 70% of this amount, whichever is smaller (FIG. 7B). Finally, onset of intrinsic ventricular activation was assessed as $A-QRS_{onset}$: the interval between atrial pace spike and the onset of QRS (FIG. 7C).

Continuous variables were presented as mean values±standard deviation whereas discrete variables are presented as counts (percentages). Linear correlations were evaluated by Pearson's correlation. Possible differences between different patient groups were tested using the Kruskal-Wallis and Wilcoxon rank-sum test with Bonferroni correction consecutively. Different methods were statistically tested using a combination of Friedman test and the Wilcoxon signed rank test with a Bonferroni correction. A two-sided p-value <0.05 was considered statistically significant. The statistical analysis was performed using IBM SPSS statistics software version 21 (SPSS Inc., Chicago, Ill.).

Of the 28 included patients, 25 patients completed all measurements. Failure to acquire all measurements in these three patients occurred due to an early stop because of back pain as a result of the prolonged procedure time in one, the inability to cross the aortic bioprosthesis in one, and technical problems with the LV pressure measurement device in one patient. The baseline characteristics of the 25 patients are presented in Table 1. The patient population was a typical CRT population with mostly males, half of the patients with ischemic cardiomyopathy, reduced LVEF, and prolonged QRS duration. During the procedure, the LV lead was aimed at a postero-lateral wall and 10% of the patients were acute non-responders (maximal change in LV $dP/dt_{max}$≤10%) taking all settings into account.

FIGS. 7A-12D are graphical illustrations of results of this experimentation and the principles of operation underlying the techniques described herein for determining the value of an A-V and/or V-V delay at which to deliver CRT. For example, some of FIGS. 7A-12D provide comparisons of the determination of an A-V delay based on D-VCG to other methods of determining an A-V delay, and illustrate some of the advantages that may be obtained by using D-VCG to determine an A-V delay based on $QRS_{ampl}$ or $QRS_{area}$. Although FIGS. 7A-12D are discussed within the context of system 18 and IMD 14 of FIG. 1, the features described with respect to these figures are not limited to such examples but may be applicable to any system for employing the techniques described herein.

FIGS. 7A-7C are graphical illustrations of intrinsic activation of a right ventricle during LV-only pacing at different A-V delays, as determined by several different methods. In FIG. 7A, a visual analysis ($A-RV_{vis}$) of a 12-lead ECG reflecting RV-only pacing at different AV-delays is illustrated. In this example, CRT first was delivered according to a 40 ms A-V delay. The A-V delay at which CRT was delivered incrementally was increased until a change in the morphology of the QRS complex was observed, as the A-V delay that produces a substantial change in the amplitude of the QRS complex indicates significant fusion of the pacing pulse and the intrinsic activation of the non-paced ventricle. In other examples, this technique may be performed by delivering CRT according to a relatively long A-V delay, and decrementing the A-V delay until a change in the morphology of the QRS complex is observed. In the example of FIG. 7A, this change in QRS morphology is visible at an A-V delay around 140-150 ms indicating contribution of intrinsic activation of the RV. In this example, delivery of CRT according to an A-V delay of approximately 150 ms may provide significant fusion of the delivered pacing pulse with the intrinsic activation of the RV. As described above, the A-$RV_{vis}$ method of determining A-V delay may result in significant improvement in hemodynamic response, although its reliance on clinician evaluation of an ECG limits its applicability to clinical settings. Thus, the ~150 ms value of the A-V delay determined by A-$RV_{vis}$ provides a basis for comparison of other methods of determining A-V delay, such as A-$RV_{aCRT}$, A-$QRS_{onset}$, and $QRS_{ampl}$ or $QRS_{area}$ derived from a D-VCG. Methods that closely approximate the A-V delay determined by A-$RV_{vis}$ may provide a similar extent of fusion of the delivered pacing pulse with the intrinsic activation of the RV, whereas methods that result in a longer A-V delay than the A-V delay determined by A-$RV_{vis}$ may provide fusion to a lesser extent.

In the example of FIG. 7B, the value of an A-RV delay was determined using the AdaptivCRT™ algorithm and compared to the ~150 ms value determined by A-$RV_{vis}$. The AdaptivCRT™ algorithm uses a formula that estimates the A-RV delay as the onset of contribution of intrinsic right ventricular activation (A-$RV_{aCRT}$). In the context of an implantable medical device such as IMD 14, this algorithm may also be embodied, for example, in C code stored in a non-transitory form in memory 104 of IMD 14. As shown in FIG. 7B, the AdaptivCRT™ algorithm was used to determine an A-RV delay in various regions of heart 10, including the apex of right ventricle 42 and the RVOT. Lead $V_1$ was used to detect atrial pacing and the EGM signals of the RV lead, which was placed either in RV 42 of the RVOT. Using the AdaptiveCRT™ algorithm, A-$RV_{aCRT}$ was determined by pre-empting the delay between atrial activation and RV sensing by 40 ms or taking 70% of this amount, whichever was smaller. In this example, the A-$RV_{aCRT}$ was determined to be 169 ms at the apex of RV 42 and 158 ms at the RVOT. Thus, the use of AdaptiveCRT™ algorithm to determine an A-V delay is at least partially site-dependent, and results in longer A-V delay values than are obtained with A-$RV_{vis}$.

In the example of FIG. 7C, the value of an A-RV delay was determined using an A-$QRS_{onset}$ method, which may evaluate an interval between an atrial pace spike and the onset of the QRS complex. All twelve ECG leads were used to determine the location of the atrial pace-spike as well as the onset of the QRS complex, but for illustration purposes only lead $V_1$ is displayed in FIG. 7C. In this example, determination of the A-RV delay using the A-$QRS_{onset}$ method resulted in an A-RV delay value of 205 ms, a significantly longer delay than that determined by either of A-$RV_{vis}$ or the AdaptiveCRT™ algorithm.

Figure 8:
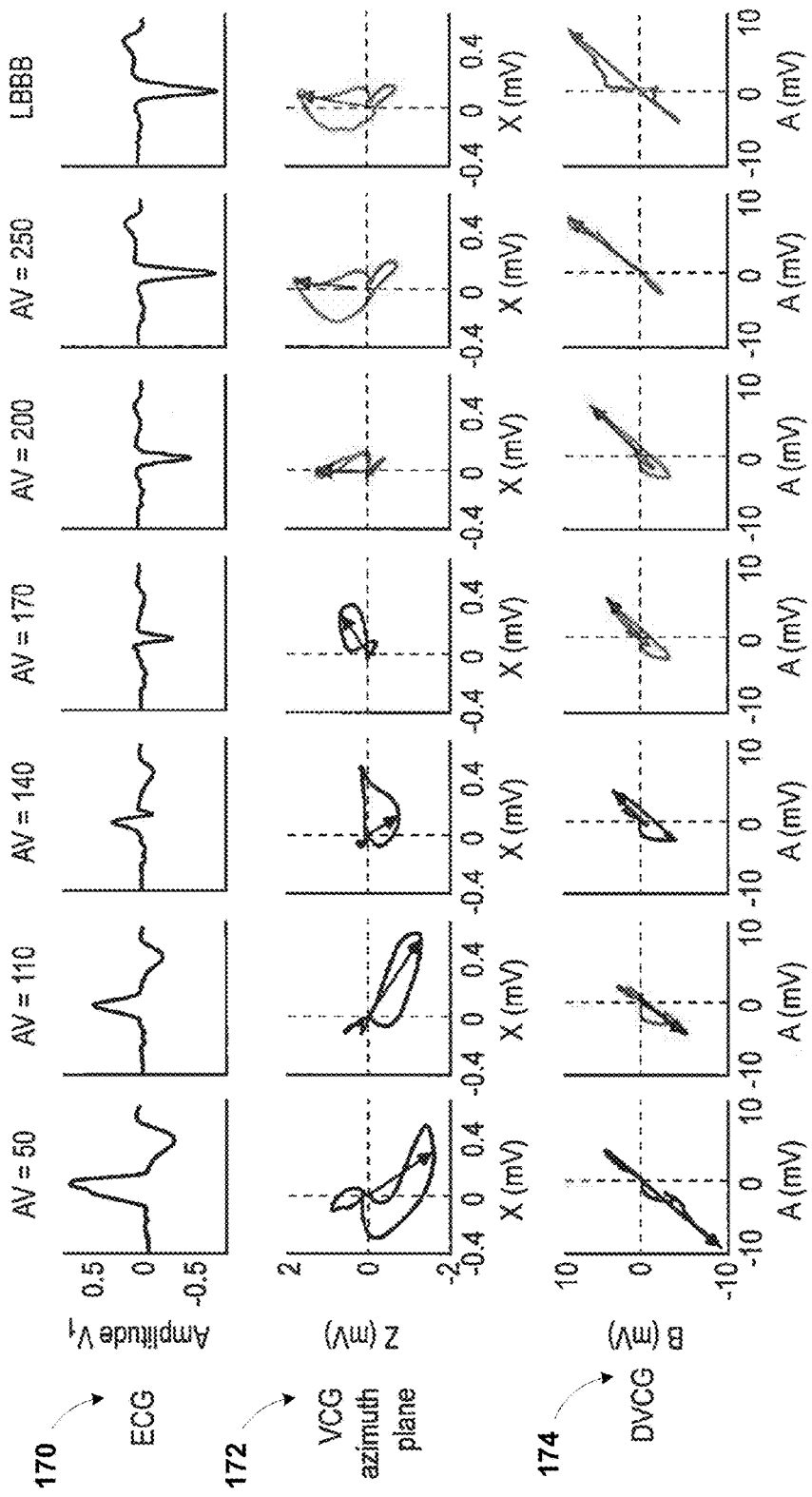
FIG. 8 is a graphical illustration of an ECG, a VCG and a D-VCG during LV pacing at different A-LV delays.

FIG. 8 is a graphical illustration of an ECG, a VCG, and a D-VCG during LV pacing at different A-V delays. As shown in ECG 170, increasing A-V delays during LV pacing, lead V1 changed from a positive to a negative QRS polarity of ECG 170 between an A-V delay of 140 ms and an A-V delay of 170 ms. These changes may be caused by increasing fusion between the paced LV wave front and the intrinsic activation wave front starting from the right bundle branch (RBB). As shown with respect to VCG 172, the A-V delay at which changes in the angle of the QRS vector occurred corresponded to the A-V delay at which a change in polarity was observed with ECG 170, although with VCG 172 this is illustrated by the vector loop extending towards the front during LV pacing and towards the back during LBBB in an angle change of ~180°. Similarly, the angle of the maximal QRS vector extracted from the D-VCG changed by ~180°. As illustrated in FIG. 8, the shapes of D-VCG loops 174 were similar to VCG loops 152, though more irregular and narrower.

Figure 9:
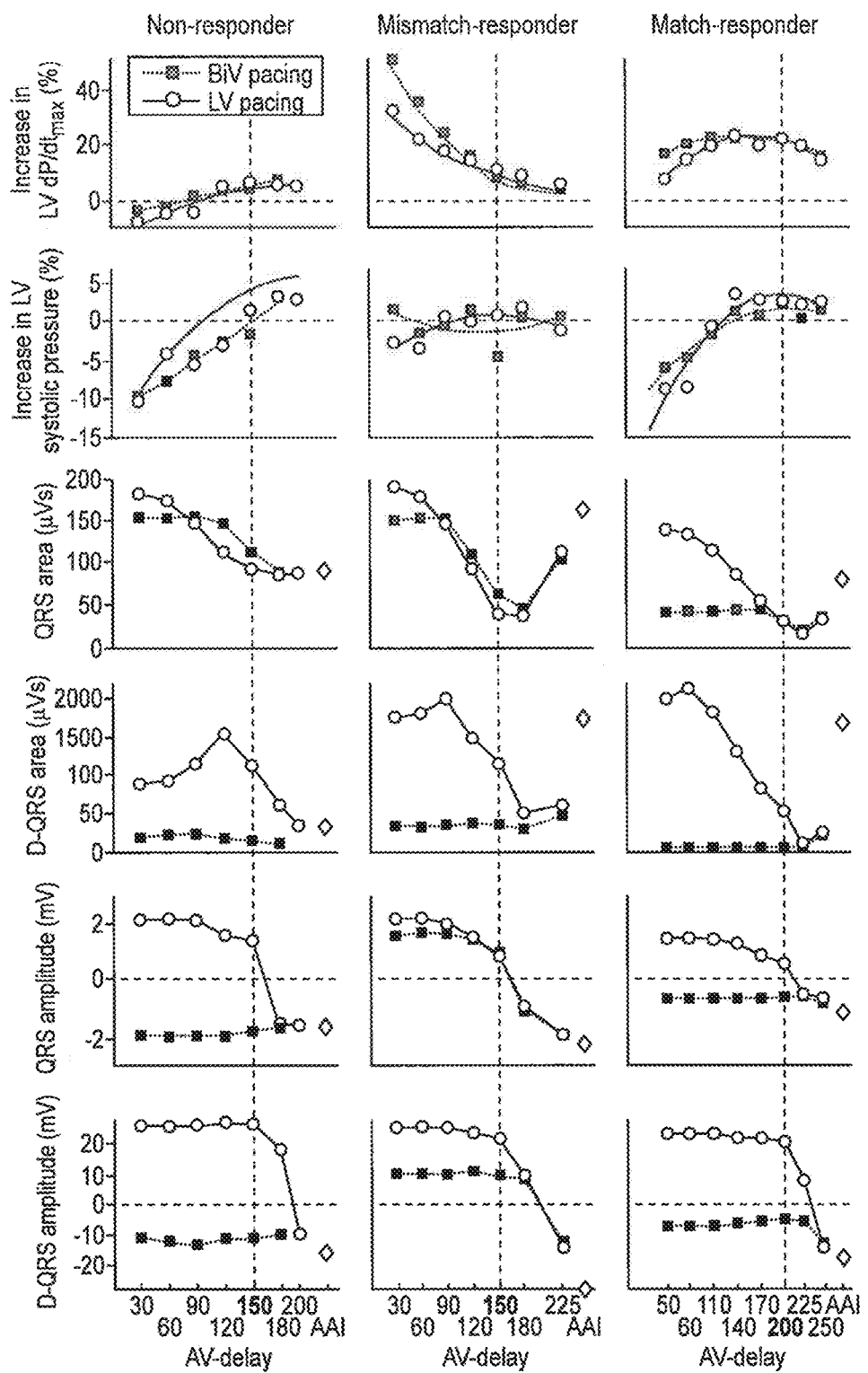
FIG. 9 is a graphical illustration of D-QRS (device-QRS) amplitude, QRS amplitude, D-QRS area, QRS area, systolic pressure and LVdP/dtmax acquired from electrodes of an implantable medical device for non-responder patients, mismatch-responder patients, and match-responder patients.

FIG. 9 is a graphical illustration of D-QRS (device-QRS) amplitude, QRS amplitude, D-QRS area, QRS area, systolic pressure and LVdP/$dt_{max}$ acquired from electrodes of an implantable medical device for non-responder patients, mismatch-responder patients, and match-responder patients. Within the entire cohort three subgroups of patients were identified based on their hemodynamic response to LV pacing: non-responders (increase in LV dP/$dt_{max}$≤10% during LV pacing protocol (n=7)); mismatch-responders in whom the LV dP/$dt_{max}$ increased>10%, but with highest LV dP/$dt_{max}$ occurring at very short AV-delays and at a different A-V delay then the highest $LVP_{syst}$ (n=8); and match-responders in whom the maximal increase in LV dP/$dt_{max}$ occurred at the same A-V delay as maximal $LVP_{syst}$ (n=10). In all three examples the A-V delay during LV pacing corresponding to the lowest VCG- and D-VCG-derived $QRS_{area}$ predicted the highest $LVP_{syst}$ quite well, even in the non-responder. Due to the mismatch between $LVP_{syst}$ and LV dP/$dt_{max}$ in the 'mismatch-responders', the AV-delay with the lowest $QRS_{area}$ did not predict the AV-delay accompanied by the highest LV dP/$dt_{max}$, because the highest LV dP/$dt_{max}$ was observed at very short AV-delay.

In the responders, the moment of onset of contribution of RV activation as determined by A-$RV_{vis}$ matched well to the A-V delay during the LV pacing that resulted in the highest $LVP_{syst}$. Importantly, A-$RV_{vis}$ corresponded with the longest A-V delay at which $QRS_{AMPL}$ was still positive. Therefore, the VCG derived $QRS_{AMPL}$ could also be used to find the delay between atrial activation and onset of contribution of ventricular activation (A-$RV_{VCG}$), especially since the transition was quite steep.

During the BiV pacing protocol, almost no changes were observed for $QRS_{area}$ and $QRS_{AMPL}$, especially, as expected, during pace settings with A-V delays shorter than the patients' A-$RV_{vis}$ (FIG. 9 rows 4 and 6). For the D-$QRS_{area}$ and D-$QRS_{AMPL}$ there were also no observable changes at A-V delays longer than A-$RV_{vis}$.

In an attempt to explain the different hemodynamic responses to LV pacing, the baseline characteristics of the three different subject groups were compared. It was observed that the match-responder group had a lower baseline LVEF and LV dP/$dt_{max}$ than the non-responder group. Furthermore, there was a trend towards a lower baseline $QRS_{area}$ for the non-responder patients (P=0.06 compared to mismatch-responder group; P=0.10 compared to match-responder group). The only observed difference between the mismatch and match responder groups was the lack of patients with ischemic cardiomyopathy (ICM) in the mismatch-responder group, while in the match-responder group 70% of the patients had ICM.

FIGS. 10A-10D are graphical illustrations of VCG- or D-VCG-derived QRS areas indicative of an A-V delay resulting in high LV systolic pressure. Overall, throughout the LV pacing protocol there was a good agreement between the surface VCG and D-VCG derived $QRS_{area}$ (R=0.74) and $QRS_{ampl}$ (R=0.80). The VCG or D-VCG derived QRS areas were able to predict the AV-delay resulting in highest LV systolic pressure with reasonable accuracy (FIGS. 10A and 10C), but not the A-V delay resulting in highest LV dP/dt$_{max}$ since the mismatch responders show a remarkable LV dP/dt$_{max}$ improvement at very short A-V delays (FIGS. 10B and 10D). The D-QRS$_{area}$ had a slightly higher off-set in an appropriate A-V delay according to LVP$_{syst}$ than QRS$_{area}$. As shown, the performance of predicting appropriate A-V delay was similar for CRT responders and non-responders.

In the responders, the moment of onset of contribution of RV activation as determined by A-RV$_{vis}$ matched well to the AV-delay during the LV pacing that resulted in the highest LVP$_{syst}$. Importantly, A-RV$_{vis}$ corresponded with the longest AV-delay at which QRS$_{ampl}$ was still positive. Therefore, the VCG derived QRS$_{ampl}$ could also be used to find the delay between atrial activation and onset of contribution of ventricular activation (A-RV$_{VCG}$).

Figure 11:
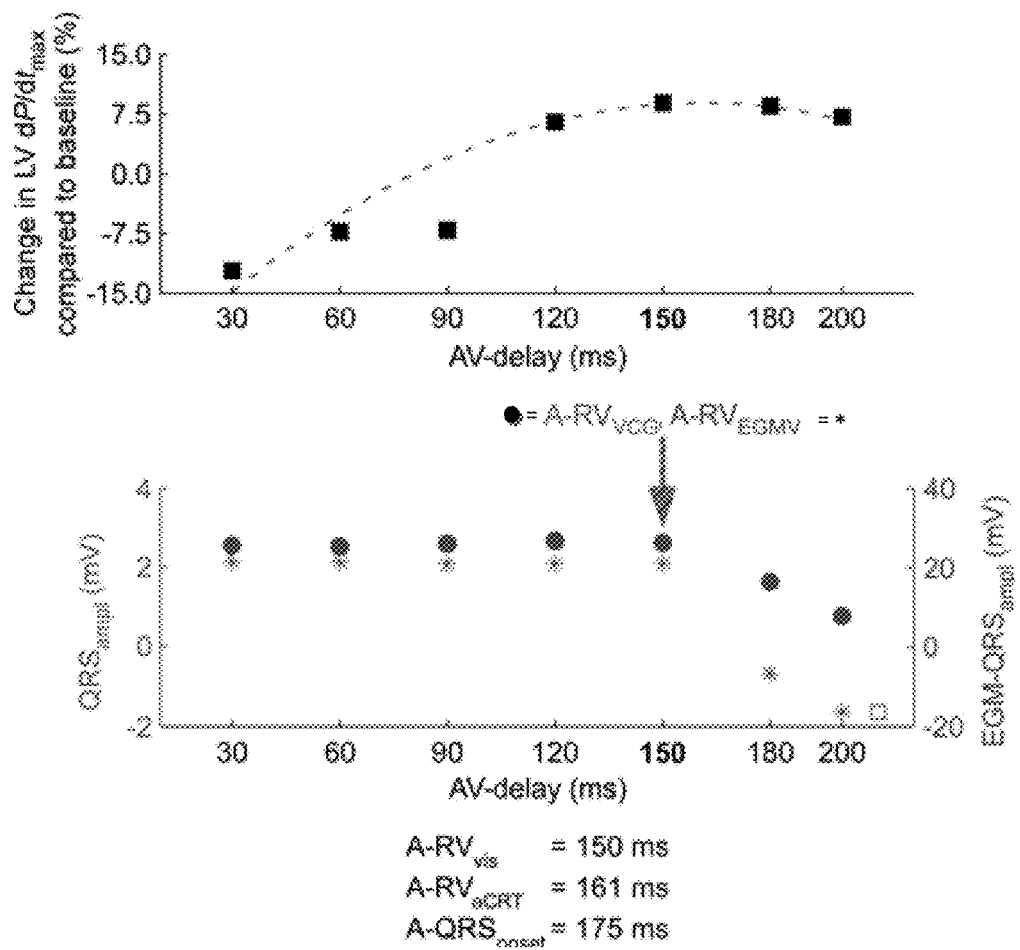
FIG. 11 is a graphical illustration of the course of a $QRS_{ampl}$ derived from a three-dimensional VCG or a two-dimensional D-VCG.

FIG. 11 is a graphical illustration of the course of a QRS$_{ampl}$ derived from the three-dimensional VCGs and two-dimensional D-VCGs (referred to in FIG. 11 as EGM QRS amplitude or EGM vectorloop QRS amplitude) over a range of A-V delay values. Also shown in FIG. 11 are the changes in LV dP/dt$_{max}$ corresponding to the increases in A-V delay. As shown, the maximal increase in LV dP/dt$_{max}$ occurred at an AV-delay of 150 ms. This maximal increase corresponded to the last AV-delay at which the QRS$_{ampl}$ extracted from both the three-dimensional VCG or a two-dimensional D-VCG corresponded to A-RV$_{vis}$, which was also 150 ms for this patient. Similar observations could be made for the other patients. This indicates that A-RV may be extracted from a three-dimensional VCG (A-RV$_{VCG}$) and two-dimensional D-VCG (A-RVD-VCG) by finding the longest AV-delay at which the QRS$_{ampl}$ was equal to the observed QRS$_{ampl}$ during LV-only pacing at a very short A-V delay.

FIGS. 12A-12D are graphical illustrations of hemodynamic responses of patient 8 to CRT delivery at settings with an AV-delay equal to the A-V delays determined according to the methods A-RV$_{vis}$, A-RV$_{D-VCG}$, A-RV$_{VCG}$, A-RV$_{aCRT}$, and A-QRS$_{onset}$. In FIGS. 12A and 12B, performances of the various algorithms are shown according to a highest measured LV dP/dt$_{max}$ for A-RV$_{vis}$, A-RV$_{D-VCG}$, A-RV$_{VCG}$, A-RV$_{aCRT}$, and A-QRS$_{onset}$. In FIGS. 12C and 12D, LVP$_{syst}$ during LV pacing with an AV-delay equal to the calculated A-RV delays is shown for A-RV$_{vis}$, A-RV$_{VCG}$, A-RV$_{aCRT}$, and A-QRS$_{onset}$. Although values for LVP$_{syst}$ are not illustrated for A-RV$_{D-VCG}$ in FIGS. 12C and 12D, an A-RV$_{D-VCG}$ may provide an approximation of an A-RV$_{VCG}$, as shown in FIGS. 12A and 12B and as discussed above. Thus, it should be understood that the LVP$_{syst}$ values shown in FIGS. 12C and 12D may also be representative of expected LVP$_{syst}$ values for A-RV$_{D-VCG}$.

To derive the data presented in FIGS. 12A-12D, the acute haemodynamic response to CRT was assessed by invasive LV pressure measurements in groups of patients receiving CRT according to one of the methods A-RV$_{vis}$, A-RV$_{VCG}$, A-RV$_{aCRT}$, and A-QRS$_{onset}$. From the LV pressure measurements, the systolic LV pressure (LVP$_{syst}$) and the rate of LV pressure rise (LV dP/dt) curves was determined. The LVP$_{syst}$ and maximum LV dP/dt (LV dP/dt$_{max}$) was determined per heart beat and averaged for the complete measurement period. In the illustrated examples, ventricular pacing measurements were alternated by baseline measurements (AAI pacing). After each transition, at least 10 seconds were used to let the pressure stabilize after which the LV pressure was measured for at least 10 seconds without any premature ventricular contractions. In order to identify the AV-delay with the largest increase in LV dP/dt$_{max}$ or LVP$_{syst}$ a parabola was fitted to the data.

The longer AV-delay found using A-QRS$_{onset}$ resulted in a significantly lower increase in LV dP/dt$_{max}$ than using the other four methods (A-RV$_{vis}$, A-RV$_{aCRT}$, A-RV$_{D-VCG}$ and A-RV$_{VCG}$; FIG. 12A). Furthermore, A-RV$_{vis}$, A-RV$_{D-VCG}$ and A-RV$_{VCG}$ resulted in a comparable increase in LV dP/dt$_{max}$, while A-RV$_{aCRT}$ led to a lower increase in LV dP/dt$_{max}$ compared to A-RV$_{vis}$, A-RV$_{D-VCG}$ and A-RV$_{VCG}$ (both P<0.05). These differences between either A-RV$_{vis}$, A-RV$_{D-VCG}$ or A-RV$_{VCG}$ and A-RV$_{aCRT}$ were also present at the individual level (FIG. 12B). Absolute changes in LVP$_{syst}$ were smaller, but there was still a trend towards lower LVP$_{syst}$ using A-RV$_{aCRT}$ compared to A-RV$_{vis}$ and A-RV$_{VCG}$ (FIGS. 12C and 12D).

As shown in FIGS. 12A and 12B, the outcome for D-VCG resembles the outcome for VCG. In some examples, the VCG or D-VCG may be used to determine the exact onset of intrinsic RV activation (A-RV$_{VCG}$) and thus to assist in individualized LV fusion pacing. Using this A-RV$_{VCG}$ the adaptive CRT algorithm can be individualized even further, leading to a possible improvement in hemodynamic response.

In some examples, an AdaptivCRT™ algorithm-based method for determining an A-V delay may be adapted for use with a VCG or D-VCG. This may be accomplished in several ways. For example, a single determination, at time of implant or shortly thereafter, using the regular ECG, from which a maximal VCG vector may be calculated. This vector may be determined during pacing a range of A-V delays. In the example of LV-pacing, the A-V delay at which a detected morphology change in the vector reflects a patient-specific A-V delay. Additionally or alternatively, an patient-specific A-V delay such as an A-RV may be calculated using AdaptivCRT™, and the difference between an A-RV$_{VCG}$ value and an A-RV$_{aCRT}$ then may be programmed into the device. This would require only to add the option of inputting a constant delay (positive or negative) on the A-RV as determined by AdaptivCRT™. In another example, a D-VCG may be determined from the pacing leads of IMD 14, as shown in FIG. 2. Alternatively, only a single electrogram may be determined.

In order to provide pseudo-continuous updates to an A-V delay using an AdaptivCRT™ algorithm-based method adapted for use with a VCG or D-VCG, a technique may be carried out as follows. For example, it may be assumed that, during daily activities such as rest, exercise, or sleep, A-RV changes much more than the conduction between the RV and LV. Therefore, a modified A-RV$_{aCRT}$ may be determined in the manner already employed by an AdaptivCRT™ algorithm; e.g., by dropping a beat and determining A-RV$_{aCRT}$ in the absence of pacing. Because conduction between RV 36 and LV 40 may change over longer time (e.g., on the order of days, for example by remodeling), every now and then a true A-RV advantageously may be determined. This can be accomplished by varying AV-delay by values close to the programmed A-RV$_{aCRT}$ value to determine whether the sign change in the electrogram, indicating a change in the A-RV$_{aCRT}$, or whether the A-RV$_{aCRT}$ remains unchanged. In some examples, the improvement of a patient's hemodynamic response to CRT can be improved, on average a few percent over baseline function, but much more in individual cases. Moreover, the techniques described herein may achieve this benefit without expending additional current, as with MPP or multisite pacing, but purely by delivering fusion pacing according to frequently-updated parameters.

Figure 13:
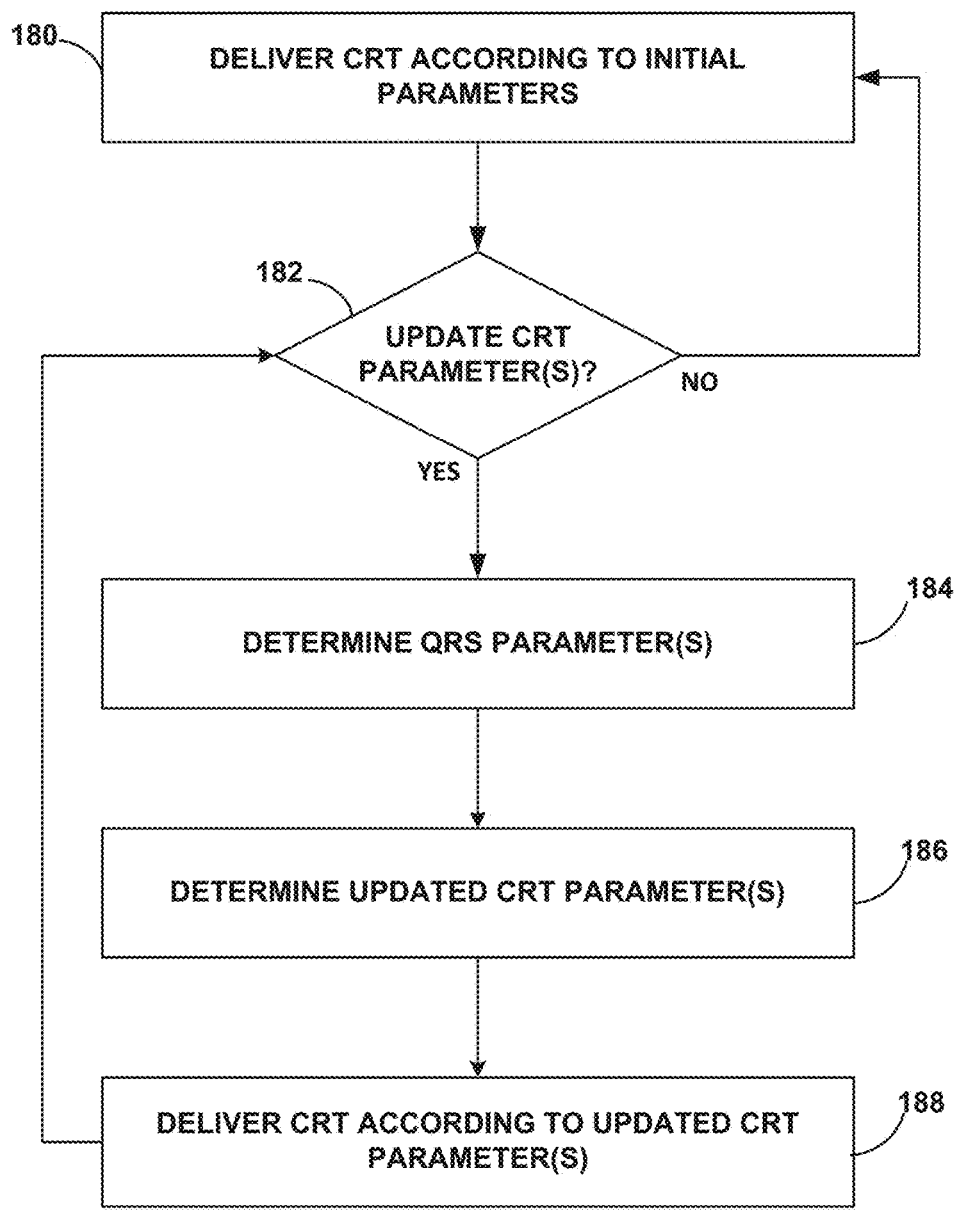
FIG. 13 is a flow diagram illustrating an example technique for delivering CRT.
Figure 14:
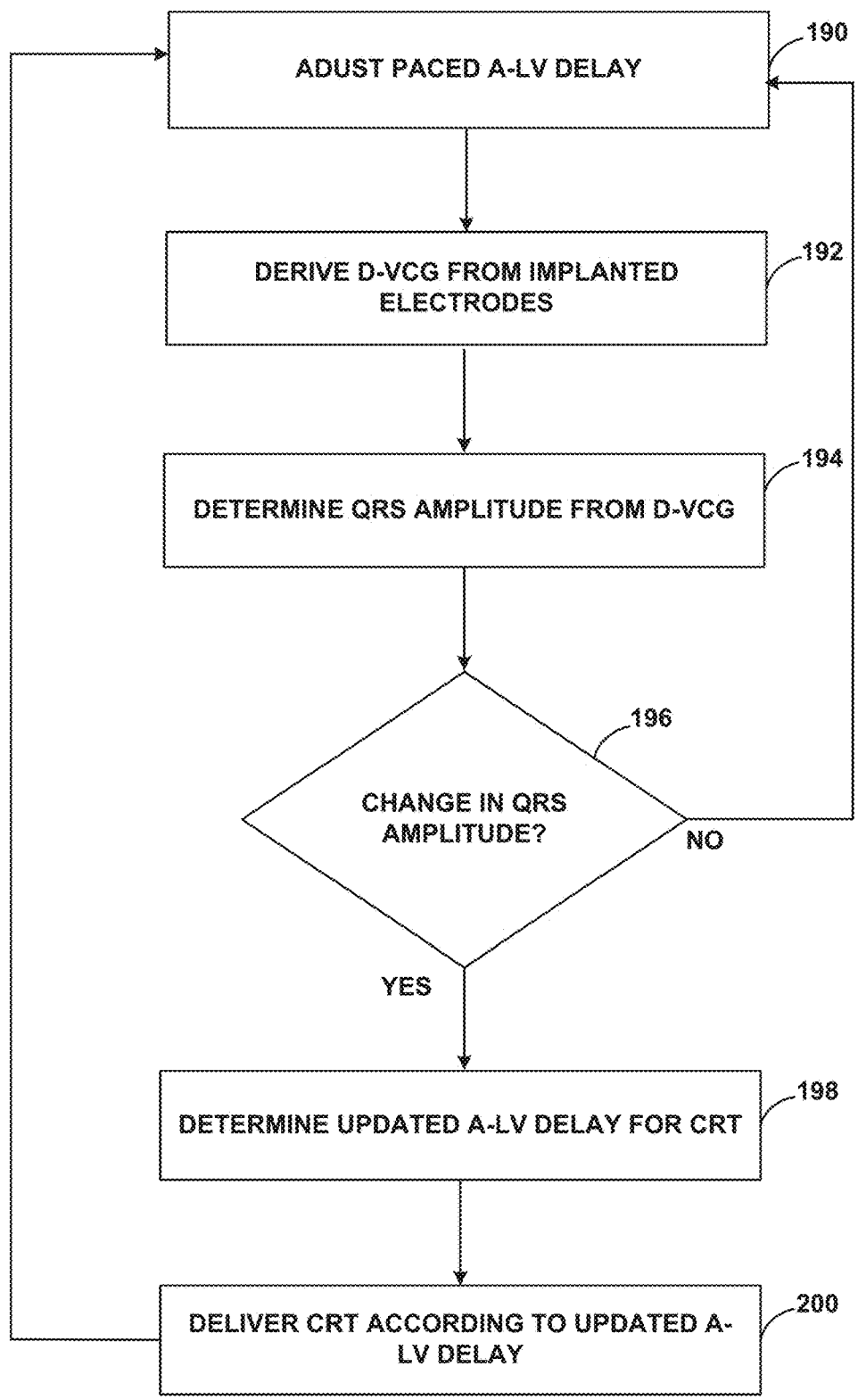
FIG. 14 is a flow diagram illustrating an example technique for determining an updated value of an A-LV delay and delivering LV fusion pacing according to the updated value of the A-LV delay.

FIGS. 13 and 14 are flow diagrams illustrating various techniques related to periodically determining an updated value for an A-V delay of a patient, based on at least one of an electrogram or a D-VCG derived from one or more implanted electrodes of an implantable medical device, and delivering CRT according to the updated A-V delay in accordance with examples of this disclosure. As described herein, the techniques illustrated FIGS. 13 and 14 may be employed using one or more components of system 18, including one or more implanted and/or external processors. Although described as being performed by IMD 14, the techniques of FIGS. 13 and 14 may be performed, in whole or in part, by processors and memory of other devices of a medical device system, as described herein.

FIG. 13 is a flow diagram illustrating an example technique for determining whether to update a patient-specific value of one or more CRT parameters, such as electrode selection, A-V delay, or V-V delay by which CRT is delivered to patient 8, determining an updated value of the CRT parameter based on one or more of the techniques described herein, and delivering CRT according to one or the updated value of the parameter. In some examples, IMD 14 may deliver CRT according to one or more initial parameters (e.g., factory settings) as part of a start-up phase of treatment following the implantation of IMD 14 within patient 18 for a period of time, such as until prompted to begin automatically updating the value of the parameter by a user, or until an initial post-implantation period of time has elapsed.

In such examples, IMD 14 may deliver CRT according to a first parameter value (180) until control of control and timing system 102 of IMD 14 determines that one or more CRT parameters, such as the A-V delay, by which CRT is delivered is to be updated (182). Control and timing system 102 may make this determination based on user instructions or an expiration of a period of time, as noted above. In the latter example, the period of time may be predetermined, and may be on the order of minutes, hours, or days. In some other examples, the period of time may be shorter, such as several times per minute or roughly once per cardiac cycle, so as to provide updates to the CRT parameters on a nearly-continuous or pseudo-continuous basis.

In still other examples, control and timing system 102 may determine an updated CRT parameter value based on sensed patient parameters in addition to or instead of the expiration of a predetermined period of time. For example, one or more components of IMD 14, such as one or more mechanical sensors (e.g., the aforementioned accelerometers, a heart-rate monitor, or one or more gyroscopes) may determine a change in an activity level of patient 8. That is, input signal processing circuit 108 of IMD 14 may detect when patient 8 begins resting, exercising, sleeping, or otherwise exhibits significantly increased or decreased physical activity, which may lead to a change in the intrinsic conduction of heart 10. Upon determining that patient 8 exhibits a change in activity level, which may exceed a threshold value, control and timing system 102 may cause IMD 14 to determine an updated parameter value (182), regardless of whether a predetermined period of time has elapsed.

In order to determine an updated CRT parameter value, control and timing system 102 may execute one or more of the techniques described herein. For example, control and timing system 102 may control therapy delivery system 106 of IMD 14 to deliver pacing pulses at increasing or decreasing A-V delay values, and may obtain one or more electrograms from one or more unpaced electrodes of leads 16, 32, and 52. For each pacing pulse so delivered, a two-dimensional D-VCG illustrating a resulting QRS complex may be constructed by two plotting bipolar EGM-vectors against each other, as described above with respect to FIG. 2. Once a D-VCG has been constructed for each test A-V delay, control and timing system 102, or any other processing circuitry included in IMD 14 or associated with system 18 may analyze the D-VCGs to determine the value of the CRT parameter, e.g., A-V delay, at which a change in the morphology (e.g., an amplitude or area) of a QRS complex represented by the D-VCG vector loop occurs (184). This parameter value may be selected as the updated parameter value by which IMD 14 will deliver CRT during the next predetermined time period, or until a change in the activity level of patient 8 is detected (186). Control and timing system 102 then may control therapy delivery system 106 of IMD 14 to deliver CRT to heart 10 according to the updated A-V delay (188).

FIG. 14 is a flow diagram illustrating an example technique for updating a patient-specific value of an A-LV delay by which CRT, e.g., left-ventricular fusion pacing, is delivered to patient 8 by adjusting a paced A-LV delay, deriving a QRS amplitude from one or more electrograms (EGMs) or D-VCGs obtained from the electrodes of IMD 14, determining whether the paced A-LV delay resulted in a change in a QRS amplitude of a QRS complex, updating the A-LV delay at which to deliver CRT, and delivering CRT accordingly. For example, when control and timing system 102 controls IMD 14 to determine an updated value of an A-LV delay, IMD 14 may deliver pacing pulses according to paced A-LV delays of increasing or decreasing durations. In some examples, the first paced A-LV delay may be significantly shorter than an expected value of an intrinsic A-LV delay; e.g., 40 ms (190). Then, a second paced A-LV delay having a longer duration than the first A-LV delay may be delivered to heart 10 (190). Next, input signal processing circuit 108 may receive signals from one or more electrodes of leads 16, 32, and 52 and transmit corresponding data to control and timing system 102. Control and timing system 102 then may construct one or more EGMs or one or more D-VCGs from the data (192) corresponding to QRS complexes resulting from each of the first A-LV delay and the second A-LV delay (192). Control and timing system 102 then may analyze the EGMs or D-VCGs to identify a QRS amplitude associated with the QRS complexes resulting from the pacing pulses (194), and determine whether the QRS amplitudes associated with the QRS complexes differ between the QRS complex resulting from the first A-V delay and the second A-V delay (196).

If control and timing system 102 determines that the QRS amplitude resulting from the second A-LV delay differs from that resulting from the first A-LV delay (196), e.g., demonstrates a target change or decrease in amplitude, control and timing system 102 may determine that the values of the first and/or second A-LV delays are associated with fusion of intrinsic ventricular activity and the delivery of the pacing pulse and designate the value of the first or second A-LV delay as the updated A-LV delay for CRT (198). In some examples, the first, or shorter, or the A-LV delays, prior to the target decrease in QRS amplitude, is designated as the updated A-LV delay. IMD 14 then may deliver CRT according to the designated A-LV delay until a predetermined period of time has elapsed or IMD 14 determines an activity change of patient 8 (200), at which time control and timing system 102 again adjust a paced A-LV delay to determine a new updated A-V delay (190).

If control and timing system 102 determines that no difference exists between the QRS amplitudes depicted by the EGMs or D-VCGs derived from the response to the first and second A-LV delays, then the control and timing system determines a third A-LV delay, which may have a longer duration than the second A-V delay, and delivers one or more pacing pulses accordingly (190). Control and timing system 102 then may construct one or EGMs or D-VCGs corresponding to a QRS complex resulting from the delivery of CRT according to the third A-LV delay (192), analyze the EGMs or D-VCGs to identify an amplitude associated with the QRS complex (194), and determine whether the QRS amplitude resulting from the third A-LV delay differs from that resulting from the first, shorter A-LV delay (196). This process may be repeated until a paced A-LV delay is identified that corresponds to a target change, e.g., decrease, in QRS amplitude associated with a QRS complex resulting from the delivery of CRT according to a paced A-LV delay, which control and timing system 102 may designate as the updated A-LV delay (198), and CRT is delivered according to the updated A-LV delay (200).

Any of the techniques described herein may be implemented in numerous different ways. For example, where a left quadripolar ventricular lead is employed, as described herein, pacing can occur in one or more middle electrodes of the left ventricular lead while sensing occurs on the proximal- and distal-most electrodes of left ventricular lead. In one or more other embodiments, a pacing configuration may comprise a right atrial ring or subcutaneous device that has a couple of electrodes. In examples in which a subcutaneous device is used, three electrodes may be subcutaneously spaced apart (e.g., as in a REVEAL™ device or other subcutaneous master device)

One or more embodiments relate to a master device controlling a slave device (e.g., a LPD, such as the MICRA® pacemaker commercially available from Medtronic, as to when to pace in the LV). In one or more embodiments, the master-slave configuration operates by sensing the atrial activity, measuring the electrogram or electrocardiogram (e.g., measured in intrinsic rhythm like the AdaptivCRT™ algorithm.)

Various aspects of the techniques may be implemented within one or more processing circuitries, including one or more microprocessors, DSPs, ASICs, FPGAs, or any other equivalent integrated or discrete logic circuitry, as well as any combinations of such components, embodied in external devices, such as physician or patient external devices, electrical stimulators, or other devices. The terms "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processing circuitries, such as one or more DSPs, ASICs, FPGAs, general purpose microprocessors, or other equivalent integrated or discrete logic circuitry. Accordingly, the term "processing circuitry," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an IMD and external device, an integrated circuit (IC) or a set of ICs, and/or discrete electrical circuitry, residing in an IMD and/or external device.

Various aspects of the disclosure have been described. These and other aspects are within the scope of the following claims.

The invention claimed is:

1. A method for controlling delivery of cardiac resynchronization therapy (CRT) by an implantable medical device of a medical device system, the method comprising:
by one or more processors of the medical device system:
controlling the implantable medical device to deliver ventricular pacing according to a sequence of different values of at least one of A-V delay or V-V delay;
during the delivery of ventricular pacing according to the sequence, acquiring one or more electrograms, each of the one or more electrograms from a respective one of a plurality of vectors formed by a plurality of electrodes of the medical device system;
for each of the different values of the at least one of A-V delay or V-V delay, determining at least one of a QRS amplitude or a QRS area based on the one or more electrograms;
identifying a target change in QRS amplitude or QRS area between a first value of the sequence of different values of the at least one of A-V delay or V-V delay and a second value of the sequence of different values of the at least one of A-V delay or V-V delay, wherein the second value is one of a next-shortest value or a next-longest value, relative to the first value, of the sequence of different values of the at least one of A-V delay or V-V delay; and
in response to the identification of the target change, controlling the implantable medical device to deliver the ventricular pacing at a value of the at least one of A-V delay or V-V delay determined based on the identification of the target change to provide CRT.

2. The method of claim 1, wherein the target change in QRS amplitude or QRS area indicates fusion occurring between right and left ventricles.

3. The method of claim 1, wherein the target change in QRS amplitude or QRS area comprises a decrease in QRS amplitude.

4. The method of claim 1, wherein controlling the implantable medical device to deliver the ventricular pacing according to the sequence of different values of at least one of A-V delay or V-V delay comprises controlling the implantable medical device to deliver left-ventricular pacing according to a sequence of different values of A-LV delay, and wherein controlling the implantable medical device to deliver the ventricular pacing at the value of the at least one of A-V delay or V-V delay determined based on the identification of the target change comprises controlling the implantable medical device to deliver LV fusion pacing at a value of an A-LV delay determined based on the identification of the target change.

5. The method of claim 1, wherein controlling the implantable medical device to deliver the ventricular pacing at the value of the at least one of A-V delay or V-V delay determined in response to the identification of the target change comprises controlling the implantable medical device to deliver the ventricular pacing at the shorter of the first value and the second value of the sequence of different values of the at least one of A-V delay or V-V delay.

6. The method of claim 1, wherein acquiring the one or more electrograms comprises acquiring two electrograms, each of the electrograms acquired from a respective one of two vectors, the method further comprising determining, by the one or more processors, a two-dimensional vectorcardiogram from the two electrograms, wherein determining the at least one of the QRS amplitude or the QRS area based on the one or more electrograms comprises determining the at least one of the QRS amplitude or the QRS area based on the two-dimensional vectorcardiogram.

7. The method of claim 6, wherein the electrograms are bipolar electrograms, and each of the two vectors includes a first pole proximate the right ventricle and a second pole proximate the left ventricle.

8. The method of claim 1, wherein the implantable medical device comprises an implanted CRT device comprising the one or more processors and coupled to the plurality of electrodes by one or more implanted leads.

9. The method of claim 1, wherein the plurality of electrodes comprises a plurality of subcutaneous electrodes, and wherein the medical device system comprises a subcutaneously implanted master device comprising the one or more processors and the plurality of subcutaneous electrodes and a leadless pacemaker slave device configured to deliver the ventricular pacing to the left ventricle.

10. The method of claim 9, wherein the plurality of subcutaneous electrodes are implanted in a subcutaneously spaced-apart arrangement.

11. A medical device system for controlling delivery of cardiac resynchronization therapy (CRT), the system comprising:
therapy delivery circuitry configured to deliver ventricular pacing to a heart of a patient;
sensing circuitry configured to sense electrical activity of the heart via a plurality of electrodes; and
one or more processors configured to:
control the therapy delivery circuitry to deliver the ventricular pacing according to a sequence of different values of at least one of A-V delay or V-V delay;
during the delivery of ventricular pacing according to the sequence, control the sensing circuitry to acquire one or more electrograms, each of the one or more electrograms from a respective one of a plurality of vectors formed by the plurality of electrodes;
for each of the different values of the at least one of A-V delay or V-V delay, determine at least one of a QRS amplitude or a QRS area based on the one or more electrograms;
identify a target change in QRS amplitude or QRS area between a first value of the sequence of different values of the at least one of A-V delay or V-V delay and a second value of the sequence of different values of the at least one of A-V delay or V-V delay, wherein the second value is one of a next-shortest value or a next-longest value, relative to the first value, of the sequence of different values of the at least one of the A-V delay or the V-V delay; and
in response to the identification of the target change, control the therapy delivery circuitry to deliver the ventricular pacing at a value of the at least one of A-V delay or V-V delay determined based on the identification of the target change to provide CRT.

12. The system of claim 11, wherein the target change in QRS amplitude or QRS area indicates fusion occurring between right and left ventricles.

13. The system of claim 11, wherein the target change in QRS amplitude or QRS area comprises a decrease in QRS amplitude.

14. The system of claim 11, wherein the one or more processors are configured to:
control the therapy delivery circuitry to deliver left-ventricular pacing according to a sequence of different values of A-LV delay; and
control the therapy delivery circuitry to deliver LV fusion pacing at a value of an A-LV delay determined based on the identification of the target change.

15. The system of claim 11, wherein the one or more processors are configured to control the therapy delivery circuitry to deliver the ventricular pacing in response to the identification of the target change by at least controlling the therapy delivery circuitry to deliver the ventricular pacing at the shorter of the first value and the second value of the sequence of different values of the at least one of A-V delay or V-V delay.

16. The system of claim 11, wherein the one or more processors are configured to:
control the sensing circuitry to acquire two electrograms, each of the electrograms acquired from a respective one of two vectors;
determine a two-dimensional vectorcardiogram from the two electrograms; and
determine the at least one of the QRS amplitude or the QRS area based on the two-dimensional vectorcardiogram.

17. The system of claim 16, wherein the electrograms are bipolar electrograms, and each of the two vectors includes a first pole proximate the right ventricle and a second pole proximate the left ventricle.

18. The system of claim 11, further comprising:
one or more implantable leads comprising the plurality of electrodes; and
an implantable CRT device comprising a housing, and the therapy delivery circuitry, sensing circuitry, and one or more processors within the housing,
wherein the implantable CRT device is coupled to the plurality of electrodes by the one or more implanted leads.

19. The system of claim 11, further comprising:
a subcutaneously implantable master device comprising the one or more processors, the sensing circuitry, and the plurality of electrodes; and
a leadless pacemaker slave device comprising the therapy delivery circuitry configured to deliver the ventricular pacing to the left ventricle.

20. An implantable medical device system for controlling delivery of left-ventricular fusion pacing, the system comprising:
therapy delivery circuitry configured to deliver left-ventricular pacing to a heart of a patient;
sensing circuitry configured to sense electrical activity of the heart via a plurality of implantable electrodes; and
one or more processors configured to:
control the therapy delivery circuitry to deliver the left-ventricular pacing according to a sequence of different values of A-LV delay;

during the delivery of the left-ventricular pacing according to the sequence, control the sensing circuitry to acquire a plurality of electrograms, each of the electrograms from a respective one of a plurality of vectors formed by the plurality of electrodes;

determine a vectorcardiogram from the electrograms;

for each of the different values of A-LV delay, determine a QRS amplitude based on the vectorcardiogram;

identify a decrease in QRS amplitude between adjacent ones of the values of A-LV delay of the sequence, wherein the decrease in QRS amplitude indicates fusion occurring between the right and left ventricles; and in response to the identification of the decrease, control the therapy delivery circuitry to deliver the left-ventricular pacing at the shorter of the adjacent ones of the values of A-LV delay to provide CRT.

21. A system for controlling delivery of cardiac resynchronization therapy (CRT), the system comprising:

means for delivering ventricular pacing according to a sequence of different values of at least one of A-V delay or V-V delay;

means for, during the delivery of ventricular pacing according to the sequence, acquiring one or more electrograms, each of the one or more electrograms from a respective one of a plurality of vectors formed by a plurality of electrodes of the medical device system;

means for, for each of the different values of the at least one of A-V delay or V-V delay, determining at least one of a QRS amplitude or a QRS area based on the one or more electrograms;

means for identifying a target change in QRS amplitude or QRS area between a first value of the sequence of different values of the at least one of A-V delay or V-V delay and a second value of the sequence of different values of the at least one of A-V delay or V-V delay, wherein the second value is one of a next-shortest value or a next-longest value, relative to the first value, of the sequence of different values of the at least one of A-V delay or V-V delay; and means for, in response to the identification of the target change, delivering the ventricular pacing at a value of the at least one of A-V delay or V-V delay determined based on the identification of the target change to provide CRT.

22. A non-transitory computer-readable medium storing instructions for causing a processor of an implantable medical device system to perform a method for controlling delivery of cardiac resynchronization therapy (CRT), the method comprising:

controlling the implantable medical device to deliver ventricular pacing according to a sequence of different values of at least one of A-V delay or V-V delay;

during the delivery of ventricular pacing according to the sequence, acquiring one or more electrograms, each of the one or more electrograms from a respective one of a plurality of vectors formed by a plurality of electrodes of the medical device system;

for each of the different values of the at least one of A-V delay or V-V delay, determining at least one of a QRS amplitude or a QRS area based on the one or more electrograms;

identifying a target change in QRS amplitude or QRS area between a first value of the sequence of different values of the at least one of A-V delay or V-V delay and a second value of the sequence of different values of the at least one of A-V delay or V-V delay, wherein the second value is one of a next-shortest value or a next-longest value, relative to the first value, of the sequence of different values of the at least one of A-V delay or V-V delay;

in response to the identification of the target change, controlling the implantable medical device to deliver the ventricular pacing at a value of the at least one of A-V delay or V-V delay determined based on the identification of the target change to provide CRT.

* * * * *